(12) United States Patent
Schmidt et al.

(10) Patent No.: US 6,670,136 B2
(45) Date of Patent: Dec. 30, 2003

(54) EXTRACELLULAR NOVEL RAGE BINDING PROTEIN (EN-RAGE) AND USES THEREOF

(75) Inventors: Ann Marie Schmidt, Franklin Lakes, NJ (US); David Stern, Great Neck, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/826,589

(22) Filed: Apr. 5, 2001

(65) Prior Publication Data

US 2002/0106726 A1 Aug. 8, 2002

Related U.S. Application Data

(63) Continuation of application No. PCT/US99/23303, filed on Oct. 6, 1999, which is a continuation-in-part of application No. 09/263,312, filed on Mar. 5, 1999, now Pat. No. 6,555,340, which is a continuation-in-part of application No. 09/167,705, filed on Oct. 6, 1998.

(51) Int. Cl.[7] .................. G01N 33/53; C07K 14/00; C07K 16/00
(52) U.S. Cl. .................. 435/7.1; 530/324; 530/350; 530/388.1; 530/389.1
(58) Field of Search .................. 435/7.1; 530/324, 530/350, 388.1, 389.1

(56) References Cited

PUBLICATIONS

Schmidt, A.M., SD Yan, and D. Stern. (1995). The Dark Side of Glucose (News and Views). Nature Medicine 1:1002–1004,.

Wu J, Rogers L, Stern D, Schmidt AM and Chiu DTW. (1997). The soluble Receptor for Advanced Glycation Endproducts (sRAGE) ameliorates impaired wound healing in diabetic mice. Plastic Surgery Research Council, Abstract #77, p. 43,.

Schmidt, A.M., Wautier, J–1., Stern D., and Yan S.D. (1998). RAGE: a receptor with a taste for multiple ligands and varied pathophysiologic states. Hormones and Signaling 1, 41–63.

Schmidt, A.M., Vianna,M., Gerlach, M., Brett, J., Ryan, J., Kao, J., Esposito, C., Hegarty, H., Hurley, W., Clauss, M., Wang, F., Pan, Y.C., Tsang, T.C., and Stern, D. (1992). Isolation and characterization of binding proteins for Advanced Glycosylation Endproducts from lung tissue which are present on the endothelial cell surface. J. Biol. Chem. 267,14987–14997.

Brett, J, et al., (1993). Survey of the distribution of a newly–characterized receptor for AGEs in tissues. Am. J. Pathol, 143:1699–1712.

Schmidt, A–M, et al. (1994). Receptor for Advanced Glycation Endproducts (AGEs) has a central role in vessel wall interactions and gene activation in response to circulating AGE proteins. Proc. Natl. Acad. Sci. (USA), 91:8807–8811.

Sell, D., and Monnier, V. (1989). Structure elucidation of a senescene cross–link from human extracellular matrix; implication of pentoses in the aging process.J.Biol. Chem. 10 264, 21597–21602.

Vlassara, H., et al. (1995). Identification of Galectin–3 as a high affinity binding protein for Advanced Glycation Endproducts (AGE): a new member of the AGE–Receptor complex. Molecular Medicine, 1:634–646.

Schmidt, A–M, et al. (1994). Cellular receptors for Advanced Glycation Endproducts. Arterioscler. Thromb., 14:1521–1528.

Hori, O., Brett, J., Slattery, T., Cao, R., Zhang, J., Chen, J., Nagashima, M., Nitecki, D., Morser, J., Stern, D., and Schmidt, A.M. (1995). The receptor for Advanced Glycation Endproducts (RAGE) is a cellular binding site for amphoterin: mediation of neurite outgrowth and coexpression of RAGE and amphoterin in the developing nervous system. J.Biol.Chem. 270, 25752–25761.

Wautier, J.–L., et al. (1996). Interaction of diabetic erythrocytes bearing advanced glycation endproducts with the endothelial receptor AGE induces generation of reactive oxygen intermediates and cellular dysfunction. Circulation Supplement 94 (8) :4139.

*Primary Examiner*—Yvonne Eyler
*Assistant Examiner*—Janet L. Andres
(74) *Attorney, Agent, or Firm*—John P. White; Cooper & Dunham LLP

(57) ABSTRACT

The present invention provides for an isolated human EN-RAGE peptide. The present invention also provides for a method for determining whether a compound is capable of inhibiting the interaction of an EN-RAGE peptide with a RAGE peptide, which comprises: (a) admixing: (i) a RAGE peptide or an sRAGE peptide or a fragment of either thereof, (ii) an EN-RAGE peptide or a fragment thereof, and (iii) the compound; (b) measuring the level of interaction between the peptide of step (a) (i) and the peptide of step (a) (ii), and (c) comparing the amount of interaction meausred in step (b) with the amount measured between the petpide of step (a)(i) and the peptide of step (a) (ii) in the absence of the compound, thereby determining whether the compound is capable of inhibiting the interaction of the EN-RAGE peptide with the RAGE peptide, wherein a reduction in the amount of interaction in the presence of the compound indicates that the compound is capable of inhibiting the interaction. The present invention also provides for a method for inhibiting inflammation in a subject which comprises administering to the subject a compound capable of interfering with the interaction between EN-RAGE peptide and receptor for advanced glycation endproduct (RAGE) in the subject thereby inhibiting inflammation in the subject.

2 Claims, 27 Drawing Sheets

FIG. 5

ATGACTAAGCTGGAGGACCACCTGGAGGGAATCATCAACATCTTC
CACCAGTACTCCGTTCGGGTGGGGCATTTCGACACCCTCAACAAG
CGTGAGCTGAAGCAGCTGATCACAAAGGGAACTTCCCAAAACCCT
CCAGAACACCAAAGACCAACCTACCATTGACAAAATATTCCAAGA
CCTGGATGCCGATAAAGACGGAGCCGTCAGCTTTGAGGAATTCGT
AGTCCTGGTGTCCAGGGTGCTGAAAACAGCCCACATAGATATCCA
CAAAGAGTAGGTTTCCAGCAATGTTCCCAAGAAGACTTACCCTTCT
CCTCCCTGAGGCTGCTCCCCGAGGGAGAGAGAATTATAAACGTAC
TTTGGCAAATTCTTAGCAAAAAAAAAAAAAAAAA

LIGATION OF EC RAGE BY EN-RAGE MEDIATES INCREASED
CELL SURFACE EXPRESSION OF VCAM-1

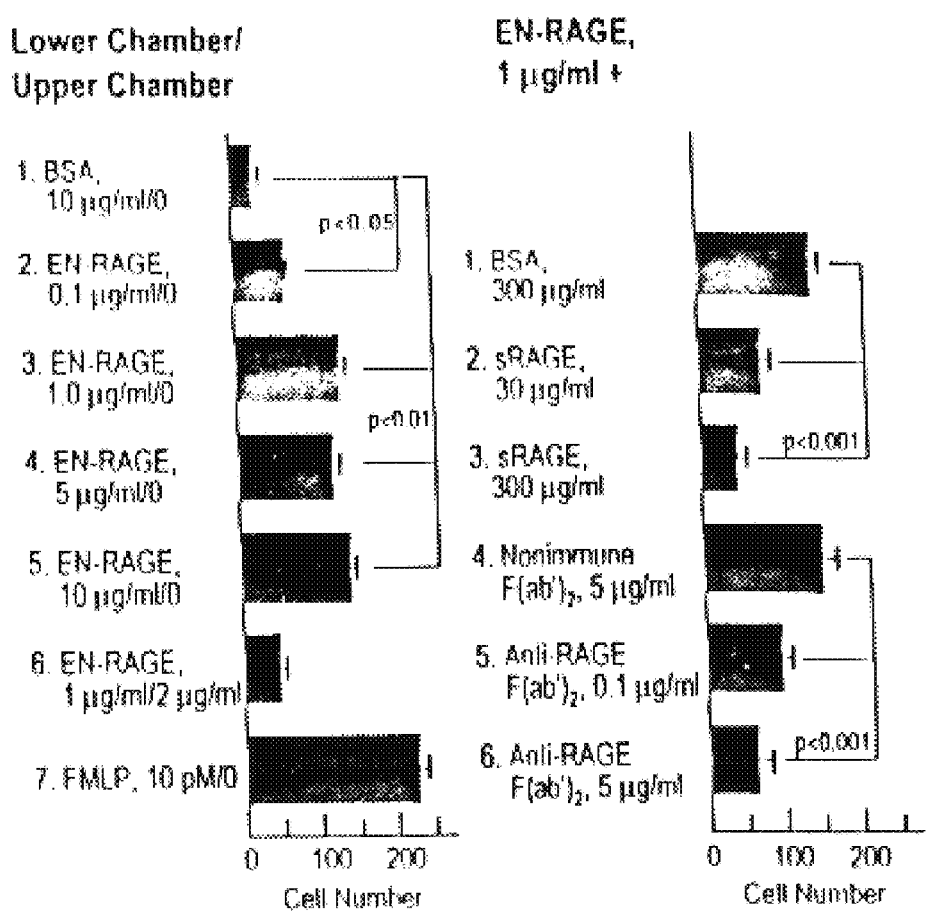

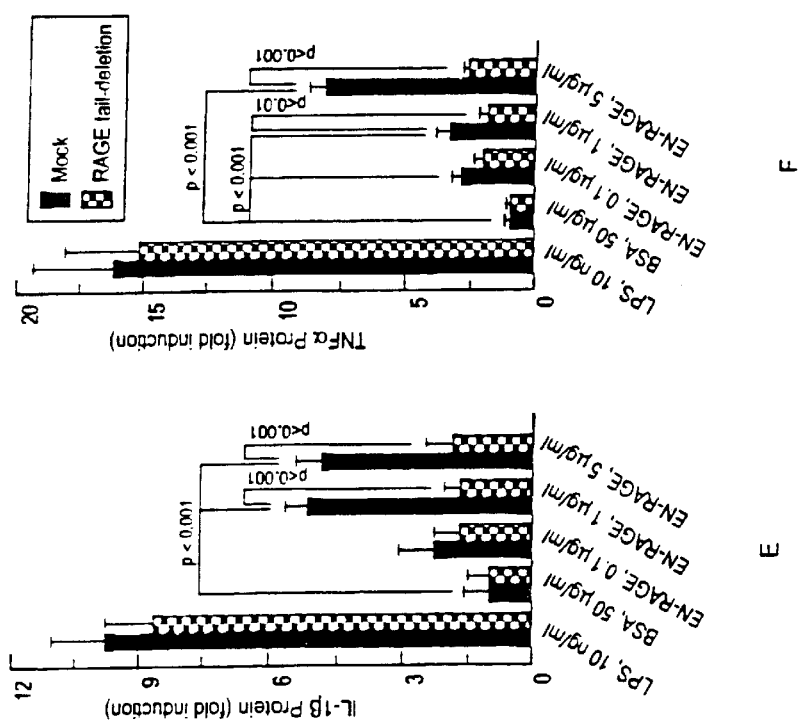
FIG. 7E-F
EN-RAGE-RAGE INTERACTION ON MPs MEDIATES INCREASED EXPRESSION OF TNF-ALPHA AND IL-1 BETA: INTACT RAGE SIGNALING IS REQUIRED FIG. 7I
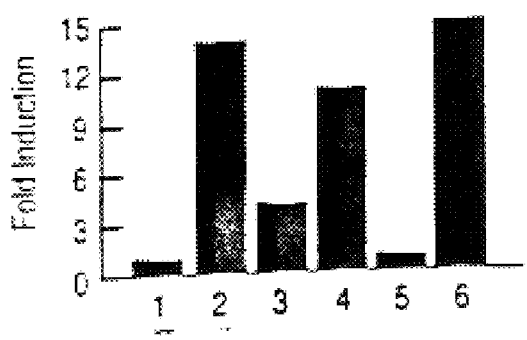
| | | | | | | |
|---|---|---|---|---|---|---|
| BSA, 5 μg/ml | + | − | − | − | − | − |
| Human S100B, 5 μg/ml | − | + | + | + | + | + |
| α-RAGE IgG, 70 μg/ml | − | − | + | − | − | − |
| Nonimmune IgG, 70 μg/ml | − | − | − | + | − | − |
| RAGE-Tail-Deleted Transfection | − | − | − | − | + | − |
| Mock Transfection | − | − | − | − | − | + |

INFUSION OF EN-RAGE INTO MICE:
INCREASED LUNG EXPRESSION OF VCAM-1 VIA RAGE

SUPPRESSION OF DTH BY BLOCKADE OF EN-RAGE/RAGE IN CF-1 MICE

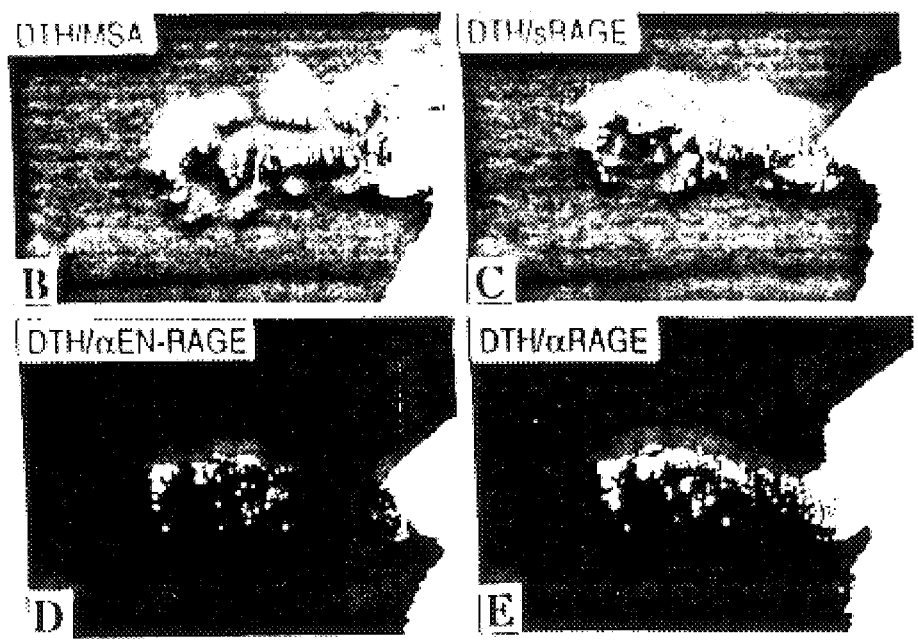
FIG.9B-E

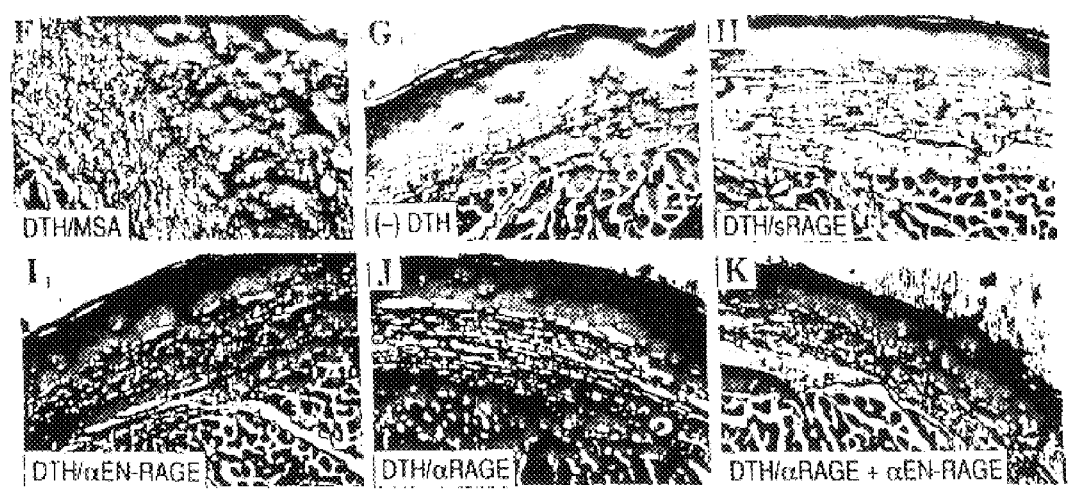
FIG. 9F-K

FIG.9L
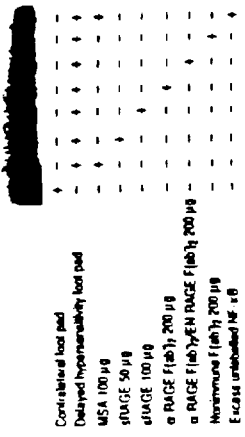
ACTIVATION OF NF-κB IS ARRESTED IN A MODEL OF DTH BY BLOCKADE OF EN-RAGE/RAGE EXPRESSION OF INFLAMMATORY CYTOKINES IS ARRESTED
IN A MODEL OF DTH BY BLOCKADE OF EN-RAGE/RAGE ACTIVATION OF COLONIC NF-κB IS ARRESTED IN A MODEL OF CHRONIC MURINE COLITIS (IL-10 NULL MICE) BY ADMINISTRATION OF SOLUBLE RAGE EXPRESSION OF PLASMA TNF-ALPHA IS SUPPRESSED IN A MODEL OF CHRONIC
MURINE COLITIS (IL-10 NULL MICE) BY ADMINISTRATION OF SOLUBLE RAGE

SEQUENCE LISTING

<160> NUMBER OF SEQ ID NOS: 6

<210> SEQ ID NO 1
<211> LENGTH: 395
<212> TYPE: DNA
<213> ORGANISM: Bovine

<400> SEQUENCE: 1

```
atgactaagc tggaggacca cctggaggga atcatcaaca tcttccacca gtactccgtt      60
cgggtggggc atttcgacac cctcaacaag cgtgagctga agcagctgat cacaaaggga     120
acttcccaaa accctccaga acaccaaaga ccaacctacc attgacaaaa tattccaaga     180
```

-continued

```
cctggatgcc gataaagacg gagccgtcag ctttgaggaa ttcgtagtcc tggtgtccag      240
ggtgctgaaa acagcccaca tagatatcca caaagagtag gtttccagca atgttcccaa      300
gaagacttac ccttctcctc cctgaggctg ctccccgagg gagagagaat tataaacgta      360
ctttggcaaa ttcttagcaa aaaaaaaaaa aaaaa                                 395
```

```
<210> SEQ ID NO 2
<211> LENGTH: 50
<212> TYPE: PRT
<213> ORGANISM: Human
<220> FEATURE:
<221> NAME/KEY: MISC_FEATURE
<222> LOCATION: (47)..(47)
<223> OTHER INFORMATION: x=any amino acid

<400> SEQUENCE: 2
```

Thr Lys Leu Glu Asp His Leu Glu Gly Ile Ile Asn Ile Gly His Gln
1               5                   10                  15

Tyr Ser Val Arg Val Gly His Phe Asp Thr Leu Asn Lys Tyr Glu Leu
                20                  25                  30

Lys Gln Leu Gly Thr Lys Glu Leu Pro Lys Thr Leu Gln Asn Xaa Lys
            35                  40                  45

Asp Gln
    50

```
<210> SEQ ID NO 3
<211> LENGTH: 90
<212> TYPE: PRT
<213> ORGANISM: Bovine

<400> SEQUENCE: 3
```

Thr Lys Leu Glu Asp His Leu Glu Gly Ile Ile Asn Ile Phe His Gln
1               5                   10                  15

Tyr Ser Val Arg Val Gly His Phe Asp Thr Leu Asn Lys Arg Glu Leu
                20                  25                  30

Lys Gln Leu Ile Thr Lys Glu Leu Pro Lys Thr Leu Gln Asn Thr Lys
            35                  40                  45

Asp Gln Pro Thr Ile Asp Lys Ile Phe Gln Asp Leu Asp Ala Asp Lys
    50                  55                  60

Asp Gly Ala Val Ser Phe Glu Glu Phe Val Val Leu Val Ser Arg Val
65                  70                  75                  80

Leu Lys Thr Ala His Ile Asp Ile His Lys
                85                  90

```
<210> SEQ ID NO 4
<211> LENGTH: 90
<212> TYPE: PRT
<213> ORGANISM: Bovine

<400> SEQUENCE: 4
```

Thr Lys Leu Glu Asp His Leu Glu Gly Ile Ile Asn Ile Phe His Gln
1               5                   10                  15

Tyr Ser Val Arg Val Gly His Phe Asp Thr Leu Asn Lys Arg Glu Leu
                20                  25                  30

Lys Gln Leu Ile Thr Lys Glu Leu Pro Lys Thr Leu Gln Asn Thr Lys
            35                  40                  45

Asp Gln Pro Thr Ile Asp Lys Ile Phe Gln Asp Leu Asp Ala Asp Lys
    50                  55                  60

```
Asp Gly Ala Val Ser Phe Glu Glu Phe Val Val Leu Val Ser Arg Val
65                  70                  75                  80

Leu Lys Thr Ala His Ile Asp Ile His Lys
                85              90

<210> SEQ ID NO 5
<211> LENGTH: 18
<212> TYPE: PRT
<213> ORGANISM: Human

<400> SEQUENCE: 5

Asp Gly Ala Val Ser Phe Glu Glu Phe Val Val Leu Val Ser Arg Val
1               5                   10                  15

Leu Lys

<210> SEQ ID NO 6
<211> LENGTH: 5
<212> TYPE: PRT
<213> ORGANISM: Human

<400> SEQUENCE: 6

Ala Gln Asn Ile Thr
1               5
```

EXTRACELLULAR NOVEL RAGE BINDING PROTEIN (EN-RAGE) AND USES THEREOF

This application is a continuation of PCT International Application No. PCT/US99/23303, filed Oct. 6, 1999, designating the United States of America, which is a continuation-in-part and claims priority of U.S. Ser. No. 09/263,312, U.S. Pat. No. 6,555,340 filed Mar. 5, 1999which is a continuation-in-part and claims priority to U.S. Ser. No. 09/167,705, filed Oct. 6, 1998, the contents of which are hereby incorporated by reference into the present application.

The invention disclosed herein was made with Government support under NIH Grant No. AG00602 from the U.S. Department of Health and Human Services, and United States Public Health Service Grant No. DK-2495, HL 56881, AG00602, DE12561. Accordingly, the U.S. Government has certain rights in this invention.

Throughout this application, various publications are referenced by author and date within the text. Full citations for these publications may be found listed alphabetically at the end of the experimental details sections for each experiment. The disclosures of these publications in their entireties are hereby incorporated by reference into this application in order to more fully describe the state of the art as known to those skilled therein as of the date of the invention described and claimed herein.

BACKGROUND OF THE INVENTION

The Receptor for AGE (RAGE) is a member of the immunoglobulin superfamily of cell-surface molecules (1–2). originally identified and characterized as a cellular receptor for glucose (aldose sugar)-modified proteins, or Advanced Glycation Endproducts (AGEs) (3–13), RAGE has subsequently been reported to interact with other ligands, in both settings of normal development and in Alzheimer's disease (14–16). In normal development, RAGE interacts with amphoterin, a polypeptide which mediates neurite outgrowth in cultured embryonic neurons. In those studies, either anti-RAGE F(ab')$_2$ or soluble RAGE (sRAGE) inhibited neurite outgrowth on amphoterin-coated matrices, but not on matrices coated with other substrates such as laminin or poly-l-lysine (3). In later studies, RAGE was identified as a receptor on neurons and microglia for amyloid-β-peptide, a polypeptide linked to the pathogenesis of neuronal toxicity and death in Alzheimer's disease.

SUMMARY OF THE INVENTION

The present invention provides for an isolated human EN-RAGE peptide. The present invention also provides for a method for determining whether a compound is capable of inhibiting the interaction c an EN-RAGE peptide with a RAGE peptide, which comprises: (a) admixing: (i) a RAGE peptide or an sRAGE peptide or a fragment of either thereof, (ii) an EN-RAGE peptide or a fragment thereof, and (iii) the compound; (b) measuring the level of interaction between the peptide of step (a) (i) and the peptide of step (a) (ii), and (c) comparing the amount of interaction measured in step (b) with the amount measured between the peptide of step (a) (i) and the peptide of step (a) (ii) in the absence of the compound thereby determining whether the compound is capable of inhibiting the interaction of the EN-RAGE peptide with the RAGE peptide, wherein a reduction in the amount of interaction in the presence of the compound indicates that the compound is capable of inhibiting the interaction. The present invention also provides for a method for inhibiting inflammation in a subject which comprises administering to the subject a compound capable of interfering with the interaction between EN-RAGE peptide and receptor for advanced glycation endproduct (RAGE) in the subject thereby inhibiting inflammation in the subject.

Figure 1:
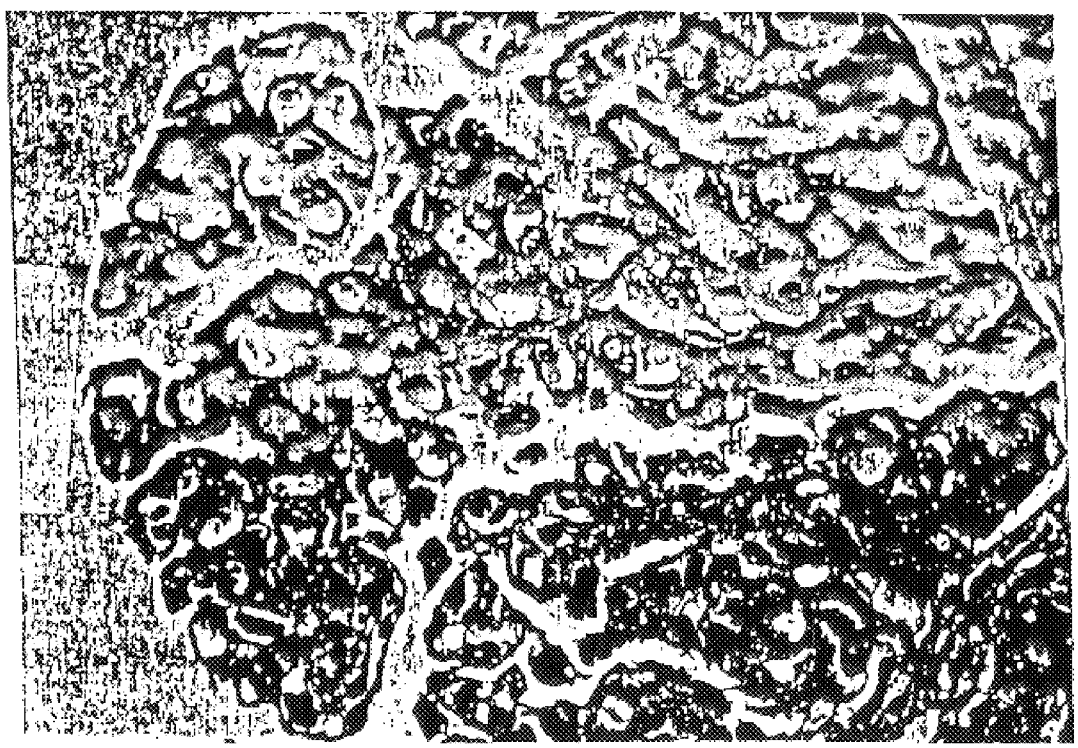
FIG. 1

Immunohistochemistry of Human Kidney (Active Lupus Nephritis)

Kidney tissue from a patient with active lupus nephritis was obtained, fixed in formalin and paraffin-embedded sections were prepared. Sections were stained with rabbit anti-RAGE IgG. Increased expression of RAGE was noted in the podocytes of the glomerulus.

FIG. 2

Incubation of HUVECs with EN-RAGE Results in Increased Cell Surface VCAM-1

Human umbilical vein endothelial cells were cultured in serum-free RPMI 1640 without endothelial cell growth factor for 24 hrs and then stimulated with EN-RAGE or bovine serum albumin (BSA); both 10 μg/ml. Where indicated, cells were pretreated with rabbit anti-human RAGE IgG, nonimmune rabbit IgG; in certain cases, EN-RAGE was pretreated with the indicated concentration of soluble RAGE (sRAGE) for 2 hrs prior to stimulation with EN-RAGE. After eight hrs stimulation with EN-RAGE, cells were fixed as described above. Cell surface ELISA employing anti-VCAM-1 IgG was performed. Statistical considerations are shown in the figure.

FIG. 3

Incubation of HUVECs with EN-RAGE Increases VCAM-1 Functional Activity: Increased Binding of Molt-4 Cells Assessment of functional VCAM-L activity was determined using $^{51}$Cr-labelled Molt-4 cells (ATCC) as described above. HUVEC were treated with either BSA (10 μg/ml) or EN-RAGE (5 μg/ml) for eight hrs. Molt-4 cells (5×10$^7$/ml) were incubated for 2 hrs in RPMI containing $^{51}$Cr (0.1 mCi). At the end of that time, cells were washed with PBS and then added to the monolayer of treated HUVEC for one hour. Unbound Molt-4 cells were removed by washing three times with PBS. Cells were then lysed in buffer containing triton-X 100 (2%) in order to release Molt-4 cell-bearing radioactivity. Statistical considerations are shown in the figure.

FIG. 4

Delayed Hypersensitivity Model Suppression of Inflammation in the Presence of Soluble RAGE CF-1 mice were sensitized with mBSA; after three weeks, mBSA was injected into the hind foot pad. Certain mice were treated with the indicated concentrations of mouse serum albumin, sRAGE or the indicated F(ab')$_2$ antibody fragments of RAGE or EN-RAGE. Inflammation score was defined as above (scale; 1–9).

FIG. 5

Nucleic Acid Sequence of Bovine EN-RAGE.

The cDNA for bovine EN-RAGE was cloned and deposited with Genbank at Accession No. AF 011757. The sequence (5' to 3') is shown in FIG. 5.

FIG. 6

Expression of EN-RAGE is Increased in Stimulated Inflammatory Cells (A–B); EN-RAGE Binds RAGE (C–D).

(Panel A) Expression of EN-RAGE is enhanced in stimulated PBMCs and Jurkat cells, but not HUVEC: Peripheral blood mononuclear cells, Jurkat E6 cells or HUVEC in standard were cultured alone or in the presence of the indicated stimuli for 12 hrs. PBMC and Jurkat E6 cells were stimulated with PMA (10 ng/ml)/ionomycin (100 ng/ml) and HUVEC were treated with TNF-a (10 ng/ml). At the end of 12 hrs incubation, cell lysates were prepared and electrophoresis/immunoblotting performed as described above employing rabbit anti-EN-RAGE IgG (2 μg/ml). Sites of primary antibody were visualized using peroxidase-conjugated antibody to rabbit IgG and ECL detection system. Molecular weight markers were run simultaneously as indicated. Results of densitometric analysis are shown. This experiment was repeated twice with analogous results.

(Panel B) Infusion of LPS into mice results in elaboration of EN-RAGE into plasma: LPS, 30 μg/kg body weight, was infused into Balb/c mice by intraperitoneal administration in the presence or absence of sPAGE (100 μg; administered 12 hrs and 1 hr prior to LPS injection) At the indicated time, blood was retrieved and plasma subjected to electrophoresis/immunoblotting for EN-RAGE using anti-EN-RAGE IgG (2 μ/ml) as above. Results of densitometric analysis are shown. This experiment was repeated twice with analogous results.

(Panel C–D) EN-RAGE binds purified RAGE (C) and BAECs (D): In C, human soluble RAGE was immobilized onto the wells of plastic dishes and in D, confluent BAECs were cultured onto tissue culture-treated wells. Radioligand binding assays were performed employing the indicated concentration of $^{125}$-I EN-RAGE in the presence or absence of excess unlabelled EN-RAGE (50 fold). In C, specific binding to purified RAGE is demonstrated, with $K_d \approx 91 \pm 29$ nM and capacity≈21±2.9 fmoles/well. In D, specific binding to BAECs is demonstrated, with $K_d \approx 90.3 \pm 34$ nM and capacity≈163±26.2 fmoles/well. Where indicated, radiolabelled EN-RAGE (100 nM) was incubated with the indicated amount of excess sRAGE two hours prior to binding assay, or wells were preincubated for two hours with the indicated concentration of rabbit nonimmune IgG, or polyclonal monospecific rabbit anti-EN-RAGE IgG or anti-RAGE: IgG prior to binding assay and results reported as % maximal specific binding ±SD of the mean. These experiments were performed at least five times with analogous results.

FIG. 7

Ligation of RAGE by EN-RAGE and S100B Results in Cellular Activation. Endothelial Cells (A–D, H).

(Panel A) Cell surface ELISA for VCAM-1: HUVEC were cultured in the presence of the indicated mediators for 8 hrs at 37° C. in the presence or absence of pretreatment with either nonimmune IgG, anti-RAGE IgG or excess soluble RAGE for two hrs. Cells were then fixed and cell surface ELISA for VCAM-1 performed employing anti-VCAM-1 IgG (4 μg/ml).

(Panel B) Molt-4 adhesion assays: HUVEC were cultured in the presence of the indicated mediators for 8 hrs. Varying concentrations (left panel) and incubation times (middle panel) for EN-RAGE were employed. After incubation, $^{51}$-chromium labelled Molt-4 cells were bound to the monolayer for one hr. At the end of that time, cells were washed in medium and disrupted in the presence of Triton X-100 (1%); the resulting material was counted in a beta counter. In the right panel, HUVEC were treated with EN-RACE, 5 μg/ml, in the presence or absence of pretreatment (2 hrs) with the indicated F(ab')$_2$, excess sRAGE or excess BSA. Results are reported as fold increase above control (treatment of the cells with BSA, 10 μg/ml). In A–B, results are reported as mean ±SD of the mean. Experiments were performed at least three times.

(Panel C) Electrophoretic mobility shift assay (EMSA): HUVEC were treated with the indicated mediators for eight hrs. In certain cases, cells were pretreated with anti-RAGE IgG and in other cases, EN-RAGE was pretreated with excess sRAGE (two hours) Certain HUVEC were transiently-transfected with a construct encoding a form of human RAGE in which the cytosolic domain was deleted or with vector alone as control (pcDNA3) prior to treatment with EN-RAGE. Nuclear extract was prepared and EMSA performed as described below. Supershift assays were performed by incubation of nuclear extract with the indicated antibody (2 μg/ml) for 45 minutes prior to EMSA. Results of densitometric analysis are shown in the inset. This experiment was repeated twice with analogous results.

Mononuclear Phagocytes (MPs) (Panel D–E)

(Panel D) Modified chemotaxis assays: Modified chemotaxis assays were performed as described. Mediators were placed in the upper or lower chamber and Molt-4 cells (which bear cells surface RAGE) for 4 hrs at 37° C. as shown. Cells which had migrated through the membranes were stained and counted in nine high-powered fields. Where indicated (right panel), cells were pretreated with the indicated F(ab')$_2$ fragments, or EN-RAGE incubated with excess sRAGE for two hrs prior to chemotaxis assay. Mean ±SD of the mean is shown. Each experiment was performed twice; in each case, six replicates per condition were employed.

(Panel E) Generation of IL-1β and TNF-a: BV-2 macrophages, either those transfected with a construct encoding the cDNA in which the cytosolic domain of RAGE was deleted, or mock-transfected cells (vector alone), were incubated with the indicated mediators for 8 hrs at 37° C. At the end of that time, supernatant was collected and ELISA for either IL-1β or TNF-a performed. Results are reported as fold induction, compared with incubation of cells with BSA alone. Mean ±SD of the mean in three experiments is shown.

PBMC and Jurkat Cells (Panel F–G)

(Panel F) Mitogenesis assay: PBMC were isolated from whole blood as described and seeded in tissue culture wells. Cells were treated with the indicated concentration of EN-RAGE for 12 hrs prior to stimulation with PHA-P. Wells were then pulsed with $^3$H-thymidine and incubated for an additional 18 hrs prior to harvesting and processing for liquid scintillation counting. In certain cases, cells were pretreated with nonimmune or anti-RAGE IgG, or EN-RAGE was pre-treated with excess sRAGE.

(Panel G) Generation of IL-2: Jurkat E6 cells were incubated with the indicated mediators for 8 hrs; supernatant was collected and ELISA for IL-2 performed. Where indicated, cells were pretreated with the indicated IgG, or EN-RAGE was pretreated with excess sRAGE. Results are reported as fold induction (compared with incubation of cells with BSA alone). In F–G, mean ±SD of at least two experiments is reported.

(Panel H) S100B activates NF-kB in HUVEC via RAGE: HUVEC were treated with the indicated mediators for eight hrs. Pretreatment with antibodies or sRAGE and EMSA were carried out as described above in (C).

FIG. 8

EN-RAGE Mediates Cellular Activation in vivo (Panel A) Expression of VCAM-1 in the lung: CF-1 mice were injected intravenously via the tail vein with EN-RACE (30 μg), BSA (30 μg) or LPS (500 μg). Twelve hrs later, lungs were rapidly harvested and extract prepared as described below for immunoblotting. Electrophoresis and immunoblotting were performed as described employing anti-VCAM-1 IgG (0.4 μg/ml). Densitometric analysis is shown. This experiment was performed twice with analogous results.

(Panel B) Mitogenesis assay: Splenocytes were retrieved from mice subjected to delayed-type hypersensitivity (see below) and examined ex vivo for response to PMA as described. For each condition, n=5 mice. Mean ±SD is shown.

FIG. 9
Blockade of EN-RAGE/RAGE Suppresses Acute Inflammation in a Model of Delayed-type Hypersensitivity (DTH). Clinical and Histological Score (A–K).

(Panel A) Inflammation score: CF-1 mice were sensitized (left groin) and challenged (left hindpaw) with methylated BSA (mBSA) as described. Where indicated, mice were pretreated by Intraperitoneal Injection with sRAGE, murine serum albumin, immune or nonimmune F(ab')$_2$ fragments, 24 and 12 hrs prior to, and 6 and 12 hrs after local challenge with mBSA. 24 hrs after injection of foot pad with mBSA, clinical and histologic score of foot pad as described was performed by two blinded investigators. In A, score (maximal of 9; no inflammation=2) is defined as the sum of the clinical and histologic score: Clinical score: 1=absence of inflammation (identical to untreated right footpad; 2=slight rubor and edema; 3=moderate rubor and edema with skin wrinkles; 4=severe rubor and edema without skin wrinkles; and 5=severe rubor and edema with toe spreading due to excessive edema. Histologic score (according to H&E studies): 1=no leukocytic infiltration and no subcutaneous edema; 2=slight perivascular leukocytic infiltrate with slight subcutaneous edema; 3=severe leukocytic infiltrate without granulomata; and 4=severe leukocytic infiltrate with granulomata. In these experiments, n=5/group. Mean ± SD of the mean is reported.

(Panel B–E) Clinical analysis: Representative mice sensitized/challenged with mBSA are shown: B=treatment with MSA; C=treatment with sRAGE, 100 µg IP per dose; D=treatment with anti-EN-RAGE F(ab')$_2$, 200 µg IP per dose; and E=treatment with anti-RAGE F(ab')$_2$, 200 µg IP per dose. (Panel F–K) H&E analysis: H&E analysis of representative footpads from mice sensitized/challenged with mBSA are shown: F=treatment with MSA; G=contralateral footpad, no DTH; H=treatment with sRAGE, 100 µg IP per dose; I=anti-EN-RAGE F(ab')$_2$, 200 µg IP per dose; J=anti-RAGE F(ab')$_2$, 200 µg IP per dose; and K=anti-EN-RAGE+anti-RAGE F(ab')$_2$, 200 µg IP per dose.

(Panel L) EMSA: Nuclear extracts were prepared from pooled hind footpads (n=3condition) and EMSA performed. Results of densitometric analysis are shown.

(Panel M) RT-PCR for IL-2 and TNF-a: RT-PCR was performed from RNA prepared from hind footpads as indicated in the figure and performed using primers for TNF-a (lanes 1 and 2) or IL-2 (lanes 4 and 5) or β-actin. Base pair markers are indicated. Lane 3 represents negative control (no DNA added during PCR).

FIG. 10
Blockade of EN-RAGE/RAGE Suppresses Chronic Colonic Inflammation in IL-10 Null Mice.

(Panel A) EMSA: Nuclear extracts were prepared from rectosigmoid colon tissue of mice treated with either sRAGE (lanes 1–6) or MSA (lanes 7–12). Densitometric analysis was performed using Image Quant/Molecular Dynamics. Mean densitometry pixel units for MSA-treated (n=6) vs sRAGE-treated mice (n=6) were 7,121.8±5,359.6 vs 1.911±1,155 units; p=0.04. (B) Assessment of Plasma TNF-a: Immediately prior to sacrifice, plasma was retrieved from IL-10 null mice and subjected to centrifugation at 800 rpm for 10 mins to obtain cellfree supernatant. ELISA for TNF-a was performed on this material according to the manufacturers' instructions. Mean values for MSA-(n=6) vs sRAGE-treated mice (n=6) were 190.5±89.0 vs 21.9±63.6 pg/ml; p=0.002.

Figure 11:
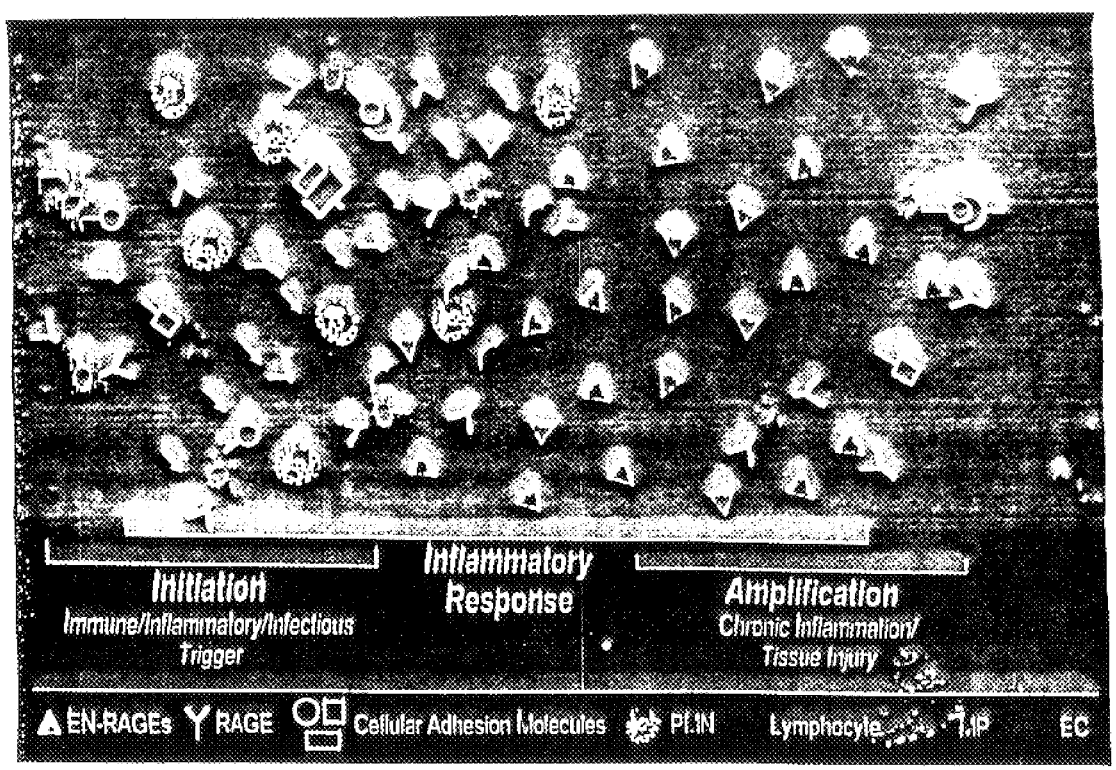

FIG. 11
Amplification of the Inflammatory Response Mediated by EN-RAGE-RAGE Axis We hypothesize that upon recruitment to sites of immune/inflammatory stimulation, inflammatory cells release EN-RAGE and EN-RAGE like S100/calgranulin molecules. These molecules may then ligate cellular RAGE, on cells such as endothelium, MPs and lymphocytes, thereby amplifying the inflammatory response via generation of key mediators of inflammation, such as adhesion molecules and cytokines.

DETAILED DESCRIPTION OF THE INVENTION

The following abbreviations are used herein: CML—carboxymethyl-lysine; AGE—advanced glycation endproduct (s); RAGE—receptor for advanced glycation endproduct (s); sRAGE—soluble receptor for advanced glycation endproduct(s); EN-RAGE—Extracellular Novel RAGE Binding Protein.

The present invention provides for an isolated human EN-RAGE peptide. In one embodiment, the isolated EN-RAGE peptide having the N-terminal amino acid sequence shown in Table 1. In another embodiment, the EN-RAGE peptide is encoded by the cDNA sequence of Genbank Accession No. AF 011 757. An isolated nucleic acid molecule encoding an EN-RAGE peptide. In one embodiment, the EN-RAGE peptide is human EN-RAGE. In another embodiment, the nucleic acid is DNA, cDNA or RNA. In one example, the nucleic acid sequence of the EN-RAGE is the sequence shown in FIG. 5 (Seq I.D. No. 1).

The present invention also provides for a replicable vector comprising the EN-RAGE nucleic acid molecule. In one embodiment, the replicable vector is a prokaryotic expression vector, a yeast expression vector, a baculovirus expression vector, or a mammalian expression vector.

The present invention also provides for a host cell comprising the replicable vector. In one embodiment, the host cell is a eukaryotic cell, a somatic cell, or a germ cell.

In another embodiment, the nucleic acid molecule of the invention may be labelled with a detectable moiety. The detectable moiety may be selected from the group consisting of: a fluorescent label, a digoxigenin, a biotin, an enzyme, a radioactive atom, a paramagnetic ion, and a chemiluminescent label.

The present invention also provides for nucleic acid molecule consisting essentially of a unique fragment of an EN-RAGE nucleic acid sequence in a 3' to 5' orientation, wherein the sequence antisense to at least a portion of a gene encoding naturally occurring EN-RAGE peptide.

The present invention also provides a composition comprising an EN-RAGE peptide or fragment thereof and a pharmaceutically acceptable carrier. In one embodiment, the pharmaceutically acceptable carrier is an aerosol, intravenous, oral or topical carrier.

The present invention also provides for an antibody immunoreactive with an epitope comprising a unique sequence of EN-RAGE.

The present invention also provides for a ribozyme which is capable of specifically cleaving EN-RAGE mRNA in a cell.

The present invention also provides for a transgenic nonhuman mammal whose germ or somatic cells contain a nucleic acid molecule which encodes an EN-RAGE peptide or a biologically active variant thereof, introduced into the mammal, or an ancestor thereof, at an embryonic stage. In one embodiment, the nucleic acid molecule which encodes EN-RAGE polypeptide is overexpressed in the cells of the mammal. In another embodiment, the nucleic acid molecule encodes human EN-RAGE peptide. In another embodiment, the active variant comprises a homolog of EN-RAGE.

The present invention also provides for a transgenic nonhuman mammal whose germ or somatic cells have been transfected with a suitable vector with an appropriate sequence designed to reduce expression levels of EN-RAGE peptide below the expression levels of that of a native mammal. In one embodiment, the suitable vector contains an appropriate piece of cloned genomic nucleic acid sequence to allow for homologous recombination. In another embodiment, the suitable vector encodes a ribozyme capable of cleaving an EN-RAGE mRNA molecule or an antisense molecule which comprises a sequence antisense to naturally occurring EN-RAGE mRNA sequence.

The present invention also provides for a method for determining whether a compound is capable of inhibiting the interaction of an EN-RAGE peptide with a RAGE peptide, which comprises: (a) admixing: (i) a RAGE peptide or an sRAGE peptide or a fragment of either thereof, (ii) an EN-RAGE peptide or a fragment thereof, and (iii) the compound; (b) measuring the level of interaction between the peptide of step (a) (i) and the peptide of step (a) (ii) and (c) comparing the amount of interaction measured in step (b) with the amount measured between the peptide of step (a) (i) and the peptide of step (a) (ii) in the absence of the compound, thereby determining whether the compound is capable of inhibiting the interaction of the EN-RAGE peptide with the RAGE peptide, wherein a reduction in the amount of interaction in the presence of the compound indicates that the compound is capable of inhibiting the interaction.

In one embodiment, the fragment of step (a) (i) is the V-domain of RAGE. In another embodiment, the fragment of step (a) (i) or (a) (ii) is synthetic. In another embodiment, the compound comprises at least a portion of naturally occurring sRAGE peptide. In another embodiment, the compound is a peptidomimetic. In another embodiment, the compound is an organic molecule. In another embodiment, the compound is a peptide, a nucleic acid or an inorganic chemical. In another embodiment, the compound is a molecule of less than 10,000 daltons. In another embodiment, the compound is an antibody or fragment thereof. In another embodiment, the compound is a mutated RAGE peptide or a fragment thereof. In another embodiment, the compound is a mutated sRAGE peptide or a fragment thereof. In another embodiment, the compound is a mutated EN-RAGE peptide or a fragment thereof. In another embodiment, the peptide of step (a) (i) is affixed to a solid surface. In another embodiment, the peptide of step (a) (ii) is affixed to a solid surface. In another embodiment, the peptide of step (a) (i) or (a)(ii) is detectably labeled. In another embodiment, the detectable label comprises fluorescence, biotin, or radioactivity.

In another embodiment, the admixing in the screening method occurs in a cell. In another embodiment, the admixing occurs in an animal.

The present invention also provides for a compound identified by the screening method described herein which compound is useful for the suppression of inflammation in a subject.

The present invention also provides for a compound identified by the method described herein which is useful for the treatment of systemic lupus erythematosus or inflammatory lupus nephritis in a subject.

The present invention provides for a previously unknown compound identified by the method described hereinabove.

The present invention also provides for a method for inhibiting inflammation in a subject which comprises administering to the subject a compound capable of interfering with the interaction between EN-RAGE peptide and receptor for advanced glycation endproduct (RAGE) in the subject thereby inhibiting inflammation in the subject.

In another embodiment, the compound is an anti-EN-RAGE antibody or a fragment thereof or an anti-RAGE antibody or fragment thereof. In another embodiment, the compound is an sRAGE peptide. In another embodiment, the compound consists essentially of the ligand binding domain of sRAGE peptide or the ligand binding domain of EN-RAGE peptide. In another embodiment, the compound is a nucleic acid molecule or a peptide. In another embodiment, the peptide is an antibody or a fragment thereof. In another embodiment, the nucleic acid molecule is a ribozyme or an antisense nucleic acid molecule. In another embodiment, the compound is a compound identified by the screening method of claim 1.

In another embodiment, the inflammation is associated with delayed hypersensitivity, accelerated athrosclerosis, or lupus nephritis. In another embodiment, the subject is a human, a primate, a mouse, a rat or a dog.

In another embodiment, the administration comprises intralesional, intraperitoneal, intramuscular or intravenous injection; infusion; liposome-mediated delivery; or topical, intrathecal, gingival pocket, per rectum, intrabronchial, nasal, oral, ocular or otic delivery. In another embodiment, the compound is administered hourly, daily, weekly, monthly or annually. In another embodiment, the effective amount of the compound comprises from about 0.000001 mg/kg body weight to about 100 mg/kg body weight.

In another embodiment, the subject is suffering from systemic lupus erythematosus, inflammatory lupus nephritis, septic shock or endotoxemia. In another embodiment, the subject is suffering from inflammation.

In a further embodiment, the subject is suffering from an autoimmune or inflammatory disorder in which recruitment of EN-RAGE-containing inflammatory cells occurs. In another embodiment, the subject is suffering from a bacterial-associated or other pathogen-associated infection.

In another embodiment, the method further comprises administering to the subject a pharmaceutically acceptable carrier during the administration of the compound. In another embodiment, the carrier comprises a diluent. In another embodiment, the carrier comprises, a virus, a liposome, a microencapsule, a polymer encapsulated cell or a retroviral vector. In another embodiment, the carrier is an aerosol, intravenous, oral or topical carrier. In another embodiment, the compound is administered from a time release implant.

The present invention also provides for a method for determining whether a compound is capable of inhibiting the ability of EN-RAGE protein to bind with a second protein which comprises: (a) admixing the EN-RAGE protein, the second protein and the compound; (b) measuring the amount of binding between the EN-RAGE protein and the second protein; and (c) comparing the amount of binding measured in step (b) with the amount of binding between EN-RAGE and the second protein in the absence of the compound, wherein a reduction in the amount of binding indicates that the compound is capable of inhibiting the ability of EN-RAGE protein to bind with the second protein.

Figure 3:
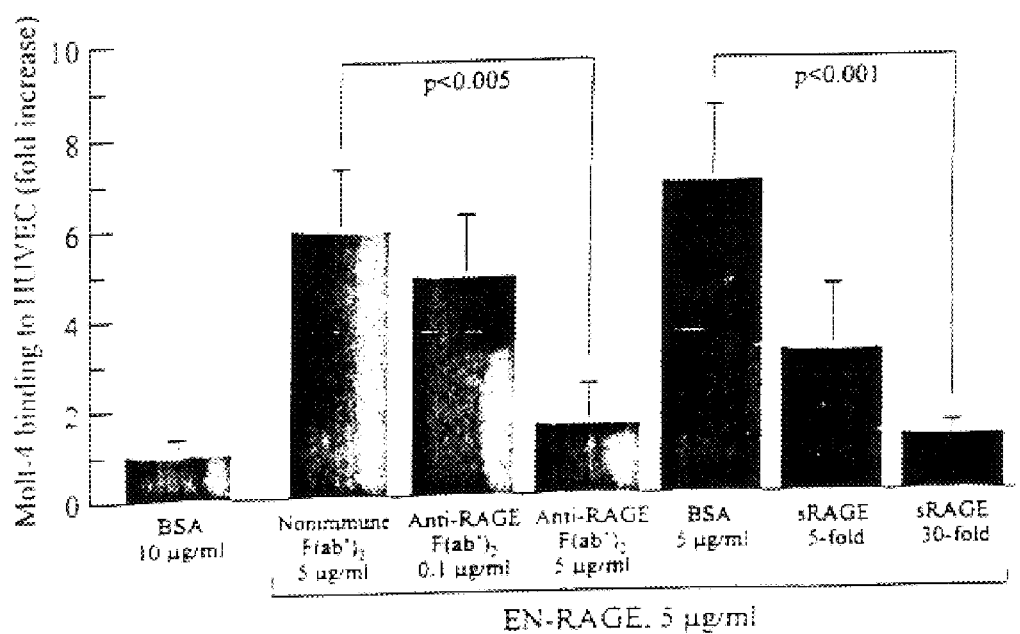
Figure 4:
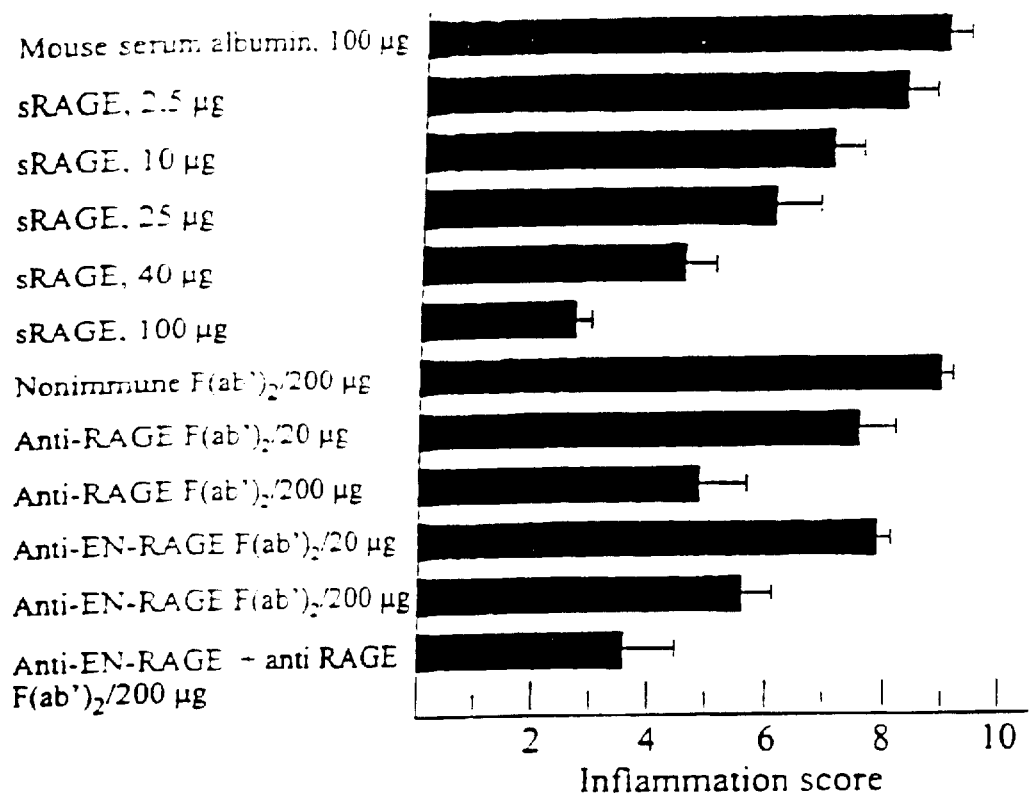

The human cDNA of RAGE is 1406 base pairs and encodes a mature protein of 404 amino acids. See FIG. 3 of Neeper et al. 1992. As used herein, "V-domain of RAGE" refers to the immunoglobulin-like variable domain as shown in FIG. 5 of Neeper, M., Schmidt, A.M., Brett, J., Yan, S.D., Wang, F., Pan, Y.C., Elliston, K., Stern, D., and Shaw, A. Cloning and expression of RAGE: a cell surface receptor for advanced glycosylation end products of proteins. J. Biol. Chem. 267:14998-15004, 1992 the conents of which are hereby incorporated by reference. The V-domain includes amino acids from position 23 to position 120 as shown in FIG. 4 of Neeper et al. (1992). The leader sequence shown is not part of the V-domain and in the human, the V-domain begins with the amino acids A-Q-N-I-T (SEQ ID NO:6). The minimum required amino acid sequence to define the AGE binding site in the RAGE protein may be much smaller than 120 amino acids.

The bovine EN-RAGE nucleic acid sequence has been cloned and has been deposited with Genbank at Accession No. AF 011757. The nucleic acid sequence of EN-RAGE is shown in FIG. 5. Homologs of EN-RAGE present in other species would be obtainable via methods known to one of skill in the art. For example, sequences unique to the bovine EN-RAGE nucleic acid cDNA sequence may be used as probes to screen a human cDNA library in order to obtain the human homolog.

Ligands for RAGE such as AGEs (CML-modified AGEs) and p12, a proinflammatory cytokine, activate inflammatory cells. This has been shown in mice. These activation effects are blocked in the presence of sRAGE. Thus, the present invention provides methods for blocking inflammation (e.g., inflammation due to immune stimulation) in a subject by administering a compound which is capable of interfering with the interaction between EN-RAGE and RAGE in a subject. Such a method would be selective for inflammation. The compound, in one example, is designed specifically as a competitive inhibitor of ligands for RAGE.

The screening assay may be carried out wherein one of the components is bound or affixed to a solid surface. In one embodiment the peptide is affixed to a solid surface. In another embodiment, the second peptide which has the sequence of the AGE binding site of RAGE is bound or affixed to a solid surface. The solid surfaces useful in this embodiment would be known to one of skill in the art. For example, one embodiment of a solid surface is a bead, a column, a plastic dish, a plastic plate, a microscope slide, a nylon membrane, etc. The material of which the solid surface is comprised is synthetic in one example.

One of the components of step (a) of the screening assay may be detectably labelled. The component (either the compound, the peptide or the V-domain or second peptide) may be labeled with a detectable moiety including a fluorescent label, a biotin, a digoxigenin, a radioactive atom, a paramagnetic ion, and a chemiluminescent label. The component may be labeled by covalent means such as chemical, enzymatic or other appropriate means with a moiety such as an enzyme or radioisotope.

In one embodiment, the subject is be a mammal. In another embodiment, the subject is a vertebrate. In a preferred embodiment, the mammal is a human. In one example, the subject is a diabetic subject. In another example of the invention, the subject is suffering from diabetes, renal failure, amyloidoses, aging or inflammation. The subject may be an obese subject as defined by the American Medical Association height and weight standards. The subject may be aged. The subject may be a human, a primate, an equine subject, an opine subject, an avian subject, a bovine subject, a porcine, a canine, a feline or a murine subject.

In one embodiment, the subject is suffering from an AGE-related disease. In another embodiment, such AGE-related disease is manifest in the brain, retina, kidney, vasculature, heart, or lung. In another embodiment, the subject is suffering from Alzheimer's disease or a disease which is manifested by AGEs accumulating in the subject. In another embodiment, the subject is suffering from symptoms of diabetes such as soft tissue injury, reduced ability to see, cardiovascular disease, kidney disease, etc. Such symptoms would be known to one of skill in the art.

The compound may be a polypeptide. The polypeptide may be a peptide, a peptidomimetic, a synthetic polypeptide, a derivative of a natural polypeptide, a modified polypeptide, a labelled polypeptide, or a polypeptide which includes non-natural peptides. The peptidomimetic may be identified from screening large libraries of different compounds which are peptidomimetics to determine a compound which is capable of preventing accelerated atherosclerosis in a subject predisposed thereto. The polypeptide may be a non-natural polypeptide which has chirality not found in nature, i.e. D-amino acids or L-amino acids.

In one embodiment, the compound is an antagonist, wherein the antagonist is capable of binding the RAGE with higher affinity than AGEs, thus competing away the effects of AGE's binding.

In another embodiment, the compound may be a ribozyme which is capable of inhibiting expression of RAGE. In another embodiment, the compound is an anti-RAGE antibody, an anti-AGE antibody, an anti-V-domain of RAGE antibody. The antibody may be monoclonal, polyclonal, chimeric, humanized, primatized. The compound may be a fragment of such antibody.

In another embodiment of the present invention, the method may further comprise administering to the subject a pharmaceutically acceptable carrier during the administration of the polypeptide. The administration may comprise intralesional, intraperitoneal, intramuscular or intravenous injection; infusion; liposome-mediated delivery; or topical, nasal, oral, ocular or otic delivery. In a further embodiment, the administration includes intrabronchial administration, anal or intrathecal administration.

The polypeptide may be delivered hourly, daily, weekly, monthly, yearly (e.g. in a time release form) or as a one time delivery. The delivery may be continuous delivery for a period of time, e.g. intravenous delivery.

The effective amount of the polypeptide may comprise from about 0.000001 mg/kg body weight to about 100 mg/kg body weight. In one embodiment, the effective amount may comprise from about 0.001 mg/kg body weight to about 50 mg/kg body weight. In another embodiment, the effective amount may range from about 0.01 mg/kg body weight to about 10 mg/kg body weight. The actual effective amount will be based upon the size of the polypeptide, the biodegradability of the polypeptide, the bioactivity of the polypeptide and the bioavailability of the polypeptide. If the polypeptide does not degrade quickly, is bioavailable and highly active, a smaller amount will be required to be effective. The effective amount will be known to one of skill in the art; it will also be dependent upon the form of the polypeptide, the size of the polypeptide and the bioactivity of the polypeptide. One of skill in the art could routinely perform empirical activity tests for a polypeptide to determine the bioactivity in bioassays and thus determine the effective amount.

In another embodiment of the present invention, the method may further comprise administering a pharmaceutically acceptable carrier to the subject during the administration of the compound. The administration may comprise intralesional, intraperitoneal, intramuscular or intravenous injection; infusion; liposome-mediated delivery; or topical, nasal, oral, ocular or otic delivery.

The compound may be administered hourly, daily, weekly, monthly, yearly (e.g. in a time release form) or as a one time delivery. The delivery or administration may be continuous delivery for a period of time, e.g. intravenous delivery.

The compound may be an sRAGE polypeptide such as polypeptide analogs of sRAGE. Such analogs include fragments of sRAGE. Following the procedures of the published application by Alton et al. (WO 83/04053), one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives of sRAGE polypeptide. Such products share at least one of the biological properties of sRAGE but may differ in others. As examples, products of the invention include those which are foreshortened by e.g., deletions; or those which are more stable to hydrolysis (and, therefore, may have more pronounced or longerlasting effects than naturally-occurring); or which have been altered to delete or to add one or more potential sites for O-glycosylation and/or N-glycosylation or which have one or more cysteine residues deleted or replaced by e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within sRAGE, which fragments may possess one property of sRAGE and not others. It is noteworthy that activity is not necessary for any one or more of the polypeptides of the invention to have therapeutic utility or utility in other contexts, such as in assays of sRAGE antagonism. Competitive antagonists may be quite useful in, for example, cases of overproduction of sRAGE.

Of applicability to polypeptide analogs of the invention are reports of the immunological property of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically-significant proteins such as viral antigens, polypeptide hormones, and the like. Included among the immune reactions of such polypeptides is the provocation of the formation of specific antibodies in immunologically-active animals [Lerner et al., Cell, 23, 309–310 (1981); Ross et al., Nature, 294, 654–658 (1981); Walter et al., Proc. Natl. Acad. Sci. USA ,78, 4882–4886 (1981); Wong et al., Proc. Natl. Sci. USA, 79, 5322–5326 (1982); Baron et al., Cell, 28, 395–404 (1982); Dressman et al., Nature, 295, 185–160 (1982); and Lerner, Scientific American, 248, 66–74 (1983). See also, Kaiser et al. [Science, 223, 249–255 (1984)] relating to biological and immunological properties of synthetic peptides which approximately share secondary structures of peptide hormones but may not share their primary structural conformation.

The compound of the present invention may be a peptidomimetic compound which may be at least partially unnatural. The peptidomimetic compound may be a small molecule mimic of a portion of the amino acid sequence of sRAGE. The compound may have increased stability, efficacy, potency and bioavailability by virtue of the mimic. Further, the compound may have decreased toxicity. The peptidomimetic compound may have enhanced mucosal intestinal permeability. The compound may be synthetically prepared. The compound of the present invention may include L-,D- or unnatural amino acids, alpha, alpha-disubstituted amino acids, N-alkyl amino acids, lactic acid (an isoelectronic analog of alanine). The peptide backbone of the compound may have at least one bond replaced with PSI-[CH=CH] (Kempf et al. 1991). The compound may further include trifluorotyrosine, p-Cl-phenylalanine, p-Br-phenylalanine, poly-L-propargylglycine, poly-D, L-allyl glycine, or poly-L-allyl glycine.

One embodiment of the present invention is a peptidomimetic compound wherein the compound has a bond, a peptide backbone or an amino acid component replaced with a suitable mimic. Examples of unnatural amino acids which may be suitable amino acid mimics include l-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

In another embodiment, the compound may be soluble RAGE (sRAGE) or a fragment thereof. Soluble RAGE is not located on the cell surface and is not associated with a cell membrane.

The subject may be a mammal or non-mammal. The subject may be a human. The subject may be a mouse, a rat, a cow, a monkey, a horse, a pig, or a dog. The subject may be a diabetic subject.

The administration of the compound may be intralesional, intraperitoneal, intramuscular or intravenous injection; infusion; liposome-mediated delivery; topical, nasal, oral, anal, ocular or otic delivery. The administration may be constant for a certain period of time or periodic and at specific intervals. The carrier may be a diluent, an aerosol, a topical carrier, an aqeuous solution, a nonaqueous solution or a solid carrier.

In the practice of any of the methods of the invention or preparation of any of the pharmaceutical compositions a "therapeutically effective amount" is an amount which is capable of preventing interaction of EN-RAGE/RAGE in a subject. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of polypeptide compositions and compounds, together with suitable diluents, preservatives, solubilizers, emulsifiers, adjuvants and/or carriers. Such compositions may be liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from the circulation and may therefore elicit relatively short-lived Pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The polypeptide or composition of the present invention may be delivered in a microencapsulation device so as to reduce or prevent an host immune response against the polypeptide or against cells which may produce the polypeptide. The polypeptide or composition of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

Pharmaceutical with Carriers

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient of the present invention (i.e., the compound identified by the screening method or composition thereof) can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In another embodiment of the present invention, the subject may have diabetes. The subject may demonstrate complications associated with diabetes. Some examples of such complications include activation of endothelial and macrophage AGE receptors, altered lipoproteins, matrix, and basement membrane proteins; altered contractility and hormone responsiveness of vascular smooth muscle; altered endothelial cell permeability; sorbitol accumulation; neural myoinositol depletion or altered Na-K ATPase activity. Such complications are discussed in a recent publication by Porte and Schwartz, Diabetes Complications: Why is Glucose potentially Toxic?, Science, Vol. 272, pages 699–700.

This invention provides a method of supressing inflammation in a subject by interfering with the ENRAGE/RAGE interaction in delayed type hypersensitivity, inflammatory colitis, chronic inflammatory bowel disease, ulcerative colitis, chronic inflammatory disorders such as atherosclerosis, Alzheimer's disease, diabetes and renal failure.

This invention provides a method of activating transcription factors through the interaction of EN-RAGE and RAGE. In one embodiment, the transcription factor is NF-κB. In another embodiment, the transcription factor is IL-1β. In another embodiment, the transcription factor is TNF-α. In another embodiment, the transcription factor is IL-2.

This invention provides a method of activating cells central to the inflammatory response though the interaction of RAGE with EN-RAGE or EN-RAGE-like molecules.

This invention provides a method of altering the cytoskeleton and cell shape, signal tranduction, and modulation of phaocytotic function including chemotaxis, phagocytosis, degranulation, and generation of reactive oxygen species.

This invention provides a method of treating Alzheimer's disease by preventing the interaction between RAGE and amyloid-β peptide.

The invention provides a method for inhibiting chronic cellular activation which comprises administering to a subject suffering from chronic cellular activation an agent capable of inhibiting the interaction of EN-RAGE and RAGE. In one embodiment, the agent is soluble RAGE, an anti-RAGE antibody, an anti-EN-RAGE antibody, or a fragment of either antibody, such as a F(ab') fragment.

The invention provides a method for the inhibition of tissue injury due to inflammation which comprises administering to a subject suffering from chronic cellular activation an agent capable of inhibiting the interaction of EN-RAGE and RAGE.

The invention provides a method for inhibiting inflammation in a subject which comprises administering to a subject suffering from inflammation an agent capable of inhibiting the interaction of EN-RAGE and RAGE in an amount sufficient to inhibit the interaction between RAGE and EN-RAGE in the subject thereby inhibiting inflammation in the subject. In one embodiment, the agent is soluble RAGE, an anti-RAGE antibody, an anti-EN-RAGE antibody, or a fragment of either antibody, such as a F(ab') fragment.

The level of cellular activation in a subject can be measured in many ways and such ways would be known to one of skill in the art. For example, one could measure the level of certain molecules which are indicative of activation, such as interleukin-1 beta, TNF-alpha, and other cytokines known to be indicative of the presence of an inflammatory response.

The invention provides a method for treating colitis in a subject which comprises administering to the subject an agent capable of inhibiting the interaction between RAGE and EN-RAGE in the subject so as to decrease chronic inflammation and thereby treat colitis in the subject.

The invention provides a method for inhibiting inflammation in a subject which comprises administering at least one agent capable of inhibiting the interaction between RAGE and EN-RAGE in the subject, thereby inhibiting inflammation in the subject. In one embodiment, both anti-RAGE antibody and anti-EN-RAGE antibody are administered.

This invention is illustrated in the Experimental Details section which follows. These sections are set forth to aid in an understanding of the invention but are not intended to, and should not be construed to, limit in any way the invention as set forth in the claims which follow thereafter.

Experimental Details

Experiment #1

The present invention provides for a new proinflammatory cytokine-like molecule (EN-RAGE)(which has some sequence similarity to the family of calgranulin molecules). EN-RAGE is a protein located inside of inflammatory cells (such as neutrophils) and which may be released by such inflammatory cells. EN-RAGE has biological activity that may be responsible for the propagation and sustainment of an inflammatory response by interacting with cellular receptor RAGE.

EXAMPLE 1

Interaction of EN-RAGE (Extracellular Novel Rage Binding Protein) with Receptor for AGE (RAGE) Perpetuates Inflammatory Responses: Suppression of Delayed-tope Hypersensitivity Reactions with Soluble Receptor for Age (sRAGE)

Expression of RAGE, the Receptor for Advanced Glycation Endproducts, is increased in the setting of inflammation. Here we report a new member of the calgranulin family of proinflammatory cytokines called EN-RAGE (or Extracellular Novel RAGE-binding protein), which interacts with RAGE on cells such as endothelial cells, to alter cellular properties in a manner consistent with perturbation. Administration of soluble RAGE (the extracellular ligand binding domain of RAGE; sRAGE) or anti-RAGE or anti-EN-RAGE F(ab')$_2$ fragments markedly attenuated inflammation in a model of delayed hypersensitivity. These data link RAGE to the inflammatory response and identify EN-RAGE and RAGE as novel targets for anti-inflammatory intervention. Soluble RAGE, furthermore, is thus a prototypic structure for the design of a new class of anti-inflammatory agents.

The Receptor for AGE (RAGE) is a member of the immunoglobulin superfamily of cell-surface molecules (1–2). Originally identified and characterized as a cellular receptor for glucose (aldose sugar)-modified proteins, or Advanced Glycation Endproducts (AGEs) (3–13), RAGE has subsequently been reported to interact with other ligands, in both settings of normal development and in Alzheimer's disease (14–16). In normal development, RAGE interacts with amphoterin, a polypeptide which mediates neurite outgrowth in cultured embryonic neurons. In those studies, either anti-RAGE F(ab')$_2$ or soluble RAGE (sRAGE) inhibited neurite outgrowth on amphoterin-coated matrices, but not on matrices coated with other substrates such as laminin or poly-1-lysine (3). In later studies, RAGE was identified as a receptor on neurons and microglia for amyloid-β-peptide, a polypeptide linked to the pathogenesis of neuronal toxicity and death in Alzheimer's disease.

In unpublished observations from our laboratory, we identified that increased RAGE expression was noted in the vascular and inflammatory cells of inflammatory lesions, such as in the kidney tissue from patients with active lupus nephritis (FIG. 1). We therefore hypothesized that RAGE might interact with alternative ligand(s) in that setting in order to, perhaps, participate in the inflammatory response.

Herein, the findings demonstrate that RAGE interacts with a molecule with close homology to calgranulin C. We have termed this molecule, EN-RAGE (Extracellular Novel RAGE binding protein) and show that EN-RAGE:RAGE interaction activates cells such as endothelial cells which are importantly involved in the inflammatory response. In a model of murine delayed hypersensitivity, administration of soluble RAGE (sRAGE), which contains the ligand interaction domain, inhibits the development of cellular activation and inflammation. These findings identify RAGE as a new target for anti-inflammatory intervention.

Materials and Methods

Isolation and Purification of EN-RAGE

Bovine lung acetone powder (SIGMA®) was subjected to solubilization in buffer containing tris (0.02 M, pH 7.4); NaCl (0.15 M); octyl-β-glucoside (1%); and protease inhibitors (PMSF and aprotinin). After serial chromatography onto SP sepharose (Pharmacia LKB®), and affi-gel 10 resin (BIO-RAD®) to which had been adsorbed purified soluble human RAGE (prepared from a baculovirus expression system), RAGE-binding proteins were identified based on a screening assay employing immobilized column fraction (Nunc Maxisorp dishes) (NUNC®) and $^{125}$-I-labelled sRAGE as above. After elution with heparin-containing buffer (1 mg/ml), positive fractions were identified. RAGE-binding proteins were subjected to sequence analysis.

Cloning of EN-RAGE. The cDNA for EN-RAGE was cloned from a bovine lung library and placed into a baculovirus expression system. In this system, EN-RAGE, which lacks a leader sequence, was synthesized within Sf9 cells. EN-RAGE was then purified after solubilization of the cells in detergent-containing buffer, and sequential purification on hydroxylapatite and heparin-containing resins. The final product displayed a single band on Coomassie-stained SDS-RAGE gels and was devoid of endotoxin after chromatography onto Detoxi-gel columns (PIERCE®). Absence of detectable endotoxin was confirmed using limulus amebocyte assay (SIGMA®).

Sequence Analysis. After SDS-RAGE identified an ≈12 kDa polypeptide with RAGE-binding activity, the gel band was eluted according to previously-published methods (17). The published method was modified by addition of a final wash of two aliquots (0.1 ml each) of guanidine (5.0 M), urea (5.0 M), trifluoroacetic acid (0.2%), acetonitrile (10%), and Zwittergent 3-08 (1.0%) (Calbiochem) to ensure that protein was completely washed from the filter. Amino-terminal sequence analysis was performed. Automated Edman degradation was carried out employing an HP-G1005A sequencer (Hewlett Packard Analytical Instruments). In order to obtain internal sequence, the gel bands were treated as above for elution, except that the extraction buffer contained half the usual amount of SDS (1). Endoproteinase Lys-C (1 μg) (Boehringer Mannheim) was added and the sample incubated overnight. The digest was then fractionated by microbore HPLC (Michrom Bioresources) on a 1 mm×50 mm PLRP-S column (Polymer Laboratories, Ltd.). The gradient utilized was 2% per minute from acetonitrile (5–75%) in trifluoroacetic acid (0.1%) and fractions were collected at 3 second intervals. Absorbance was monitored at 214 nm and fractions that corresponded to chromatographic peaks were then subjected to sequence analysis.

Endothelial Cell Activation. Human umbilical vein endothelial cells were isolated, characterized and maintained as previously described (18). Cells were cultured in serum-free RPMI 1640 without endothelial cell growth factor for 24 hrs and then stimulated with the indicated concentrations of EN-RAGE. Where indicated, cells were pretreated with rabbit anti-human RAGE IgG, nonimmune rabbit IgG; in certain cases, EN-RAGE was pretreated with the indicated concentration of soluble RAGE (sRAGE) for 2 hrs prior to stimulation with EN-RAGE. After eight hrs stimulation with EN-RAGE, cells were fixed with paraformaldehyde (2%) for 30 mins, washed twice with PBS, treated with PBS containing non-fat dry milk (5%) and BSA (2.5%) to block nonspecific binding sites on the cell surface. Cell surface ELISA employing anti-VCAM-1 IgG (Santa Cruz Biotechnologies, Santa Cruz, Calif.) was performed. Assessment of functional VCAM-1 activity was determined using $^{51}$Cr-labelled Molt-4 cells (ATCC) as previously described (10).

Delayed Hypersensitivity Model. A murine model of delayed hypersensitivity was established based on previously-published studies (19). Female CF-1 mice (Charles River laboratories), 6 weeks of age, were sensitized by subcutaneous injection over the left inguinal lymph node of an emulsion (0.1 ml) containing methylated BSA (mBSA; 25 mg/ml; SIGMA®), NaCl (0.9%), dextran (5–40×10$^6$ MW; 50 mg/ml; SIGMA®) and Freund's incomplete adjuvant (50%; ICN Biomedical). Three weeks later, the left plantar hind paw was injected subcutaneously with mBSA (0.4 mg/ml; 0.050 ml). Where indicated, mice were pretreated by intraperitoneal injection with sRAGE (indicated dose), mouse serum albumin (SIGMA®), immune or non-immune F(ab')$_2$ fragments (prepared using a kit from Pierce) 24 and 12 hrs prior to, and 6 and 12 hrs after local challenge with mBSA. 24 hrs after infection of foot pad with mBSA, clinical score of foot pad was performed; mice were then humanely sacrificed and feet fixed in formalin (10%) or frozen for further analysis. Histologic score was performed on sections of foot stained with hematoxylin and eosin (SIGMA®). The clinical score was defined as follows (scale; 1–5): 1=no inflammation and thus identical to untreated foot; 2=slight rubor and edema; 3=severe rubor and edema with wrinkling of the skin of the foot pad; 4=severe rubor and edema without wrinkling of the skin of the foot pad; and 5=severe rubor and edema resulting in spreading of the toes. The histologic score after hematoxylin and eosin staining was defined as follows (scale; 1–5): 1=no leukocytic infiltration with slight subcutaneous edema; 2=slight perivascular leukocytic infiltration with slight subcutaneous edema; 3=severe leukocytic infiltration without granulomata; and 4=severe leukocytic infiltration with granulomata.

Results

Identification of EN-RAGE. After a serial series of experiments designed to identify RAGE-binding proteins from bovine lung extract (from where RAGE was originally purified), an ≈12 kDa polypeptide was identified. Upon sequence analysis, this polypeptide was found to bear significant homology to members of the calgranulin C family of proteins (Table 1) (20–21). This class of proteins exist intracellularly within inflammatory cells. Upon release in inflamed loci, we postulated they might be able to, in turn, engage and activate other cells already recruited into the inflammatory response. Thus, this might represent an important means by which the inflammatory response might be propagated and sustained, thereby increasing the probability of cellular injury.

Figure 2:
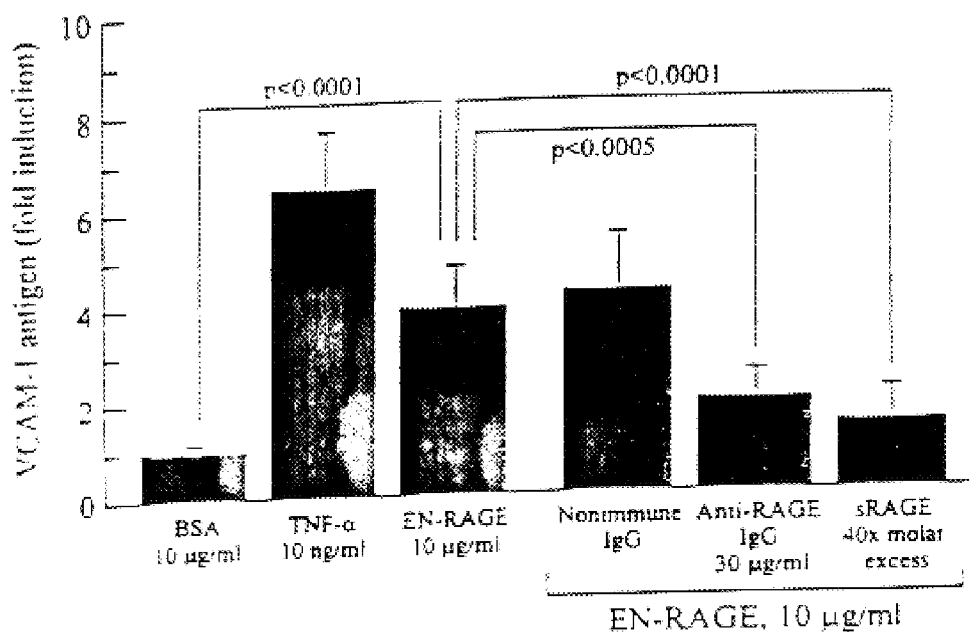

EN-RAGE Activates endothelial cells in a RAGE-dependent manner. To test this hypothesis, EN-RAGE was purified as described above and incubated with endothelial cells. Incubation of EN-RAGE with HUVEC resulted in increased cell surface Vascular Cell Adhesion Molecule-1 (VCAM-1) in a RAGE-dependent manner (FIG. 2). These data suggested that in an inflammatory focus, interaction of EN-RAGE with EC RAGE might represent a means by which to further propagate an inflammatory response. Consistent with increased VCAM-1 antigen on the surface of EN-RAGE-treated ECs, increased binding for Molt-4 cells (which bear the ligand for VCAM-1, VLA-4), ensued (FIG. 3). While incubation with either BSA or non-immune IgG did not affect the ability of EN-RAGE to activate EC VCAM-1, incubation with either sRAGE or anti-RAGE F(ab')$_2$ significantly attenuated the ability of EN-RAGE to increase Molt-4 binding to treated HUVEC.

We sought to test these hypotheses in in vivo models. We demonstrated that in diabetic mice, in which the ligand for RAGE is likely to be, at least in part, products of glycation/oxidation of proteins/lipids, the Advanced Glycation Endproducts, or AGEs, administration of the soluble, ligand-binding portion of RAGE (soluble or sRAGE), suppressed accelerated atherosclerosis in diabetic apolipoprotein E null mice (12) and improved wound healing in genetically-diabetic db+/db+ mice (22). Thus, the biologic effects of EN-RAGE in highly-inflammatory foci, such as those characterized by models of granulomatous inflammatory lesions (delayed hypersensitivity), could be suppressed in the presence of sRAGE.

To test this, we studied a model of delayed hypersensitivity (DH) in which mice were first sensitized by injection of methylated BSA (mBSA; which does not bind RAGE) over the inguinal lymph nodes of female CF-1 mice. Three weeks after sensitization, mice were challenged with mBSA by injection into the hind foot pad. An inflammation score was designed on a scale of 1–9 which included both clinical score (1–4) and histologic score (1–5) as indicated in FIG. 4.

Consistent with our hypothesis, administration of sRAGE suppressed inflammation upon injection of mBSA into the foot pad of mice previously-sensitized with mBSA over the lymph nodes, in a dose-dependent manner (FIG. 4). At a dose of 100 µg sRAGE, inflammation was markedly suppressed (p<0.01). In contrast, administration of mouse serum albumin, had no effect on the appearance of the inflammatory lesion (FIG. 4). Consistent with an important role for EN-RAGE and RAGE in the development of inflammation in this model, treatment of the mice with either anti-EN-RAGE F(ab')$_2$ or anti-RAGE F(ab')$_2$ considerably suppressed inflammation (p<0.05 in each case compared with treatment with nonimmune F(ab')$_2$. When mice were treated with both anti-EN-RAGE and anti-RAGE F(ab')$_2$, even further suppression of the inflammatory response eventuated (p<0.05 compared with treatment with nonimmune F(ab')$_2$(FIG. 4).

Discussion

The inflammation phenotype observed in delayed-type hypersensitivity reactions certainly represent the culmination of a complex interplay and contribution of multiple cell types and their cellular mediators. In the development of inflammation, an important source of the stimuli may be from the inflammatory cells themselves. Upon initial recruitment into an inflammatory locus, cells such as neutrophils and macrophages may release mediators such as those of the calgranulin family, including EN-RAGE, and propagate and sustain the inflammatory response. Such mediators, such as EN-RAGE, likely require cellular receptors to initiate events that will culminate in altered gene expression.

Our data strongly suggest that EN-RAGE-RAGE interaction is an important factor in these processes. Nearly complete suppression of inflammation was noted in the presence of sRAGE, in a dose-dependent manner. Based upon our studies, sRAGE may act as a decoy in this setting to bind EN-RAGE prior to its ability to engage RAGE-bearing cells implicated in the inflammatory response. Furthermore, in the presence of anti-RAGE/anti-EN-RAGE or anti-RAGE+anti-EN-RAGE F(ab')$_2$, substantial suppression of inflammation was observed, further indicating a role of these factors in the modulation of the inflammatory response.

It is important to note, of course, that alternate mechanisms underlying the beneficial effects of sRAGE may be operative in these settings. However, the studies noted above employing the indicated F(ab')$_2$ fragments, strongly implicate EN-RAGE and RAGE in the evolution of the inflammatory response in this setting.

In conclusion, the studies presented herein implicate RAGE centrally in the inflammatory response and identify soluble RAGE as a prototypic structure for the development of novel, anti-inflammatory agents.

Note: FIG. 5 shows the nucleic acid sequence (cDNA sequence) of bovine EN-RAGE.

called EN-RAGE, binds immobilized RAGE and endothelial (EC)/macrophage (MP) RAGE in culture wells with Kd ≈75nM, processes blocked in the presence of anti-RAGE IgG or soluble (sRAGE; the extracellular two-thirds of RAGE). In vitro, exposure of cultured ECs to EN-RAGE increased activation of NF-kB, expression of cell-surface VCAM-1 (4.3-fold compared to treatment with bovine serum albumin BSA), and adhesion of Molt-4 cells (which bear VLA-4, the counter-ligand for VCAM-1) (7-fold compared with BSA), all in a manner inhibited in the presence of anti-RAGE IgG or sRAGE. Exposure of macrophages to EN-RAGE resulted in increased chemotaxis in a RAGE-dependent manner. To test these concepts in vivo, we utilized a model of delayed hypersensitivity in mice in which footpad injections of methylated BSA (mBSA) induce localized inflammation. Pre-treatment

TABLE 1

Sequence analysis of EN-RAGE (SEQ ID NO:2) and comparison with Endo Lys C (SEQ ID NO:5), B-COAg (SEQ ID NO:3) and B-CAAF1 (SEQ ID NO:4).

```
                1                   10                  20
EN-RAGE         T K L E D H L E G I I N I G H Q Y S V R V G H F
N-TERM                          30
                D T L N K Y

Endo Lys C

B-COAg          T K L E D H L E G I I N I F H Q Y S V R V G H F
                D T L N K R

B-CAAF1         T K L E D H L E G I I N I F H Q Y S V R V G H F
                D T L N K R 31                  40                  50
EN-RAGE         E L K Q L G T K E L P K T L Q N X K D Q
N-TERM

Endo Lys C

B-COAg          E L K Q L I T K E L P K T L Q N T K D Q P T I D
                K I F Q D L

B-CAAF1         E L K Q L I T K E L P K T L Q N T K D Q P T I D
                K I F Q D L 61                  70                  80
EN-RAGE
N-TERM

Endo Lys C              D G A V S F E E F V V L V S R V L K

B-COAg          D A D K D G A V S F E E F V V L V S R V L K T A
                H I D I H K

B-CAAF1         D A D K D G A V S F E E F V V L V S R V L K T A
                H I D I H K
```

EXAMPLE 2

EN-RAGE (Extracellular Novel-RAGE Binding Protein) Activated Endothelial Cells to Mediate Inflammatory Responses The expression of Receptor for AGE (RAGE) is enhanced in inflammatory settings such as atherosclerosis and autoimmune vasculitities. We hypothesized that Receptor for AGE (RAGE) might interact with alternative ligands beyond Advanced Glycation Endproducts (AGES) in such settings. We isolated and purified an ≈12 kDa polypeptide from extract of bovine lung which bore homology to the calgranulin family of proinflammatory mediators. This polypeptide, (intraperitoneal; IP) with sRAGE prevented mBSA-mediated inflammation in a dose-dependent manner. At 100 µg IP sRAGE, the mBSA-treated foot manifested no inflammation and markedly diminished activation of NF-kB compared with mice treated with vehicle, mouse serum albumin (MSA); further, elaboration of TNF-alpha into the serum was completely prevented. Partial anti-inflammatory responses were observed upon treatment of the mice with either anti-RAGE or anti-EN-RAGE F(ab')$_2$. Nonimmune F(ab')$_2$ was without effect. Taken together, these findings indicate that ligands alternative to AGEs such as EN-RAGE activate ECs and MPs, thereby linking RAGE to the generalized inflammatory response.

EXAMPLE 3 sRAGE Results in Diminished Mortality After Endotoxemia: A Potential Treatment for Septic Shock The use of sRAGE or compounds which are capable of inhibiting the interaction of EN-RAGE and RAGE could be useful agents for the treatment of septic shock or sepsis in subjects. It has been shown that a subject given lethal doses of LPS has reduced mortality when the LPS is given in the presence of sRAGE.

sRAGE and Endotoxemia

Soluble Receptor for AGE (sRAGE) has been shown to prevent inflammation in a model of delayed-type hypersensitivity. Unlike certain anti-inflammatory-type agents, it was believed that sRAGE might exert beneficial effects when administered in the setting of endotoxemia, a prototypic result of, for example, profound gram negative bacteremia.

When uniformly lethal doses of LPS were administered to Balb/C mice (≈750 µg), administration of sRAGE (pre or post LPS injection) prevented death in ≈50% of the mice in pilot studies.

These data underscore the proposition that the potent anti-inflammatory effects of sRAGE are not associated with an untoward inclination toward morbidity/mortality due to the presence of septicemia/endotoxemia. sRAGE, therefore, may be a selective anti-inflammatory agent with selective protective effects against maladaptive inflammatory responses.

EXAMPLE 4

We induced arthritis in dba mice by sensitization with bovine collagen II. Certain mice (20) were treated with soluble RAGE, murine, 100 µg/day intraperitoneally; others (20) were treated with murine serum albumin as vehicle treatment. Half of the mice were sacrificed 6 weeks later; the remaining half were sacrificed 9 weeks later.

Data are as Follows

1. We measured the joint swelling in sRAGE vs albumin-treated mice. Joint swelling increased 2-fold in albumin-vs sRAGE-treated mice, <0.05 at both time points.
2. At the 9 week time point, plasma levels of tumor necrosis factor alpha were 3-fold higher in albumin vs sRAGE-treated mice ($p<0.05$).
3. Local injection of bovine collagen II into the ear resulted in a 2-fold increase in ear thickness in the albumin-treated mice; no change at all from baseline was noted in sRAGE-treated mice ($p<0.05$).
4. Levels of monocytes in peripheral blood were 2.5-fold lower in sRAGE-vs albumin-treated mice ($p<0.05$), suggestive of diminished inflammation.

Pending Studies: Joint Pathology and Radiographic Studies.

References

1. Schmidt, A. M., Vianna, M., Gerlach, M., Brett, J., Ryan, J., Kao, J., Esposito, C., Hegarty, H., Hurley, W., Clauss, M., Wang, F., Pan, Y. C., Tsang, T. C., and Stern, D. Isolation and characterization of binding proteins for advanced glycosylation endproducts from lung tissue which are present on the endothelial cell surface. J. Biol. Chem. 267:14987–14997, 1992.
2. Neeper, M., Schmidt, A. M., Brett, J., Yan, S. D., Wang, F., Pan, Y. C., Elliston, K., Stern, D., and Shaw, A. Cloning and expression of RAGE: a cell surface receptor for advanced glycosylation end products of proteins. J. Biol. Chem. 267: 14998–15004, 1992.
3. Schmidt, A-M, Hori, O, Brett, J, Yan, S-D, Wautier, J-L, and Stern D. Cellular receptors for advanced glycation end products. Arterioscler. Thromb. 14:1521–1528, 1994.
4. Schmidt, A. M., S D Yan, and D. Stern. The Dark Side of Glucose (News and views). Nature Medicine 1:1002–1004, 1995.
5. Yan, S-D, Schmidt, A-M, Anderson, G, Zhang, J, Brett, J, Zou, Y-S, Pinsky, D, and Stern, D. Enhanced cellular oxidant stress by the interaction of advanced glycation endproducts with their receptors/binding proteins. J. Biol. Chem. 269:9889–9897, 1994.
6. Schmidt, A-M, Yan, S-D, Brett, J, Mora, R, Nowygrod, R, and Stern D. Regulation of mononuclear phagocyte migration by cell surface binding proteins for advanced glycosylation endproducts. J. Clin. Invest. 92:2155–2168, 1993.
7. Wautier, J. L., Chappey, O,Wautier, M P, Hori, O, Stern, D, and Schmidt A M. Receptor-mediated endothelial dysfunction in diabetic vasculopathy: sRAGE blocks hyperpermeability. J. Clin. Invest. 97:238–243, 1996.
8. Miyata, T., Hori, O, Zhang, J. H., Yan, S. D., Ferran, L, Iida, Y, and Schmidt, A. M. The Receptor for Advanced Glycation Endproducts (RAGE) mediates the interaction of AGE-$b^2$-Microglobulin with human mononuclear phagocytes via an oxidant-sensitive pathway: implications for the pathogenesis of dialysis-related amyloidosis. J. Clin. Invest. 98:1088–1094, 1996.
9. Schmidt, A-M, Hasu, M, Popov, D, Zhang, J-H, Chen, J, Yan, S-D, Brett, J, Cao, R, Kuwabara, K, Gabriela, C, Simionescu, N, Simionescu, M, and Stern D. Receptor for advanced glycation endproducts (AGEs) has a central role in vessel wall interactions and gene activation in response to circulating AGE proteins. PNAS(USA) 91:8807–8811, 1994.
10. Schmidt, A M, Hori, O, Chen, J, Brett, J, and Stern, D. AGE interaction with their endothelial receptor induce expression of VCAM-1: a potential mechanism for the accelerated vasculopathy of diabetes. J. Clin. Invest. 96:1395–1403, 1995.
11. Lander, H. L., Tauras, J. M., Ogiste, J. S., Moss, R. A., and A. M. Schmidt. Activation of the Receptor for Advanced Glycation Endproducts triggers a MAP Kinase pathway regulated by oxidant stress. J. Biol. Chem. 272:17810–17814, 1997.
12. Park, L., Raman, K. G., Lee, K. J., Yan, L., Ferran, L. J., Chow, W. S., Stern, D., and Schmidt, A. M. Suppression of accelerated diabetic atherosclerosis by soluble Receptor for AGE (sRAGE). Nature Medicine 4:1025–1031, 1998.
13. Wautier J. L., Chappey O, Wautier M. P., Boval B, Stern D and A. M. Schmidt. Interaction of diabetic erythrocytes bearing advanced glycation endproducts with the endothelial receptor AGE induces generation of reactive oxygen intermediates and cellular dysfunction. Circ. 94 (8):#4139, 1996.
14. Hori, O., J. Brett, T. Slattery, R. Cao, J. Zhang, J. Chen, M. Nagashima, D. Nitecki, J. Morser, D. Stern, A. M. Schmidt. The Receptor for Advanced Glycation Endproducts (RAGE) is a cellular binding site for amphoterin: mediation of neurite outgrowth and co-expression of RAGE and amphoterin in the developing nervous system. J. Biol. Chem. 270:25752–25761, 1995.
15. Yan, S. D., X. Chen, J. Fu, M. Chen, H. Zhu, A. Roher, T. Slattery, M. Nagashima, J. Morser, A. Migheli, P.

Nawroth, G. Godman, D. Stern, and A. M. Schmidt. RAGE and amyloid-b peptide neurotoxicity in Alzheimer's disease. Nature 15 382:685–691, 1996.
16. Yan, S-D., Zhu, H., Fu, J., Yan, S-F., Roher, A., Tourtellotte, W., Rajavashisth, T., Chen, X., Stern, D. and Schmidt, A-M. Amyloid-beta peptide-RAGE interaction elicits neuronal expression of M-CSF: a proinflammatory pathway in Alzheimer's disease. Proc. Natl. Acad. Sci. 94:5296–5301, 1997.
17. Slattery, T. K. and Harkins, R. N. Techniques in protein chemistry IV, ed. Angeletti, R. H., Academic Press, San Diego, Calif., 1992.
18. Jaffe, E., Nachman, R., Becker, C., and Minick, R. Culture of human endothelial cells derived from umbilical veins. Identification by morphologic and immunologic criteria. J. Clin. Invest. 52:2745–2756, 1973.
19. Dunn, C. J., Galinet, L. A., Wu, H., Nugent, R. A., Schlachter, S. T., Staite, N. D., Aspar, D. G., Elliott, G. A., Essani, N. A., Rohloff, N. A., and Smith, R. J. Demonstration of novel anti-arthritic and anti-inflammatory effects of diphosphonates. J. Pharmacology and Experimental Therapeutics 266: 1691–1698, 1993.
20. Wicki, R., Marenholz, I., Mischke, D., Schafer, B. W., and Heizmann, C. W. Characterization of the human S100A12 (calgranulin C, p6, CAAF1, CGRP) gene, a new member of the S100 gene cluster on chromosome 1q21. Cell Calcium 20:459–464, 1996.
21. Dell'Angelica, E. C., Schleicher, C. H., and Santome, J. A. Primary structure and binding properties of calgranulin C, a novel S100-like calcium-binding protein from pig granulocytes. J. Biol. Chem. 269:28929–28936, 1994.
22. Wu J, Rogers L, Stern D, Schmidt A. M. and Chiu D. T. W. The soluble receptor for Advanced Glycation Endproducts (sRAGE) ameliorates impaired wound healing in diabetic mice. Plastic Surgery Research Council, Abstract #77, p. 43, 1997.

Experiment #2

Rage Mediates a Novel Proinflammatory Axis: the Cell Surface Receptor for S100/Calgranulin Polypeptides S100/calgranulin polypeptides are present at sites of inflammation, likely released by inflammatory cells targetted to such loci by a range of environmental cues. We report here that Receptor for AGE (RAGE) is the cell surface receptor for EN-RAGE (Extracellular Novel RAGE binding protein), and related members of the S100/calgranulin superfamily. Interaction of EN-RAGEs with cellular RAGE on endothelium, mononuclear phagocytes and lymphyocytes triggers cellular activation, with generation of key proinflammatory mediators. Blockade of EN-RAGE/RAGE quenches delayed type hypersensitivity and inflammatory colitis in murine models by arresting activation of central signalling pathways and inflammatory gene expression. These data highlight a new paradigm in inflammation and identify novel roles for EN-RAGEs and RAGE in chronic cellular activation and tissue injury.

The Receptor for Advanced Glycation Endproducts (RAGE), a member of the immunoglobulin superfamily of cell surface molecules (Schmidt et al., 1992; Neeper, et al., 1992), interacts with distinct ligands. Although RAGE was originally described as a cellular receptor for Advanced Glycation Endproducts (AGEs), the products of glycoxidation that accumulate in disorders such as diabetes and renal failure (Brownlee et al., 1988; Sell and Monnier, 1989; Reddy et al., 1995; Miyata et al., 1996 a, b), recent data indicate that an important role for RAGE is emerging in a variety of settings, both in homeostasis and in pathophysiologically-important states (Hori et al., 1995; Yan et al., 1996; Yan et al., 1997).

Consistent with an emerging paradigm that challenges the concept of one receptor interacting with one ligand, we previously noted that RAGE bound a polypeptide of _12 kDa, (Hori et al., 1995), a member of the S100/calgranulin superfamily of proinflammatory cytokines (Zimmer et al., 1995; Schafer and Heinzmann, 1996). Such molecules, likely released from activated inflammatory cells such as polymorphonuclear leukocytes, peripheral blood-derived mononuclear phagocytes and lymphocytes, have been traditionally described as accumulating in states characterized by chronic inflammation, such as inflammatory conjunctivitis (Gottsch et al., 1997; Gottsch and Liu, 1998), psoriatic skin disease (Madson, 1991), cystic fibrosis (Andersson et al., 1988), inflammatory bowel disease (Lugering et al., 1995; Schmid et al., 1995), rheumatoid arthritis (Odink et al., 1987) and chronic parasitic infection (Marti et al., 1996). Yet, to date, specific means by which polypeptides within the S100/calgranulin family potentially modulate the course of inflammatory processes were not elucidated. We report here the characterization of a 12 kDa polypeptide, termed EN-RAGE (Extracellular Novel RAGE-binding protein). Ligation of cellular RAGE by EN-RAGE and EN-RAGE-like molecules mediates activation of endothelial cells, macrophages and lymphocytes, cells central to development of the inflammatory phenotype. Consistent with the concept that EN-RAGE-RAGE interaction is a critical, proximal step in the cascade of events amplifying inflammation, administration of either soluble RAGE, or anti-RAGE/anti-EN-RAGE F(ab')$_2$ in murine models of delayed-type hypersensitivity and chronic inflammatory bowel disease, suppresses development of inflammation, with suppressed activation of NF-kB and inflammatory mediators.

Our data thus validate for the first time an important pathogenic role for EN-RAGE and EN-RAGE-like molecules in the inflammatory response. Upon recruitment of inflammatory cells to sites of autoimmune, physical or infection-mediated injury, for example, we hypothesize that release of these molecules, and their subsequent interaction with cellular RAGE, may propagate a potent series of aggravating pro-inflammatory events. Thus, these data highlight a new paradigm in inflammation and identify novel roles for EN-RAGEs and RAGE in chronic cellular activation and tissue injury.

Experimental Procedures

1. Protein Sequence Analysis

To perform sequence analysis; bands (≈12 kDa) were eluted from SDS-RAGE gels as previously described (Hori et al., 1995). Automated Edman degradation was carried out using an HP-G1005A sequencer (Hewlett Packard Analytical Instruments, Palo Alto, Calif.) Internal sequencing was performed using endoproteinase Lys-C (Boehringer Mannheim) digestion followed by microbore HPLC as described (Hori et al., 1995).

2. Molecular Cloning

Molecular cloning was performed using a bovine lung library and human lung library (Clontech, Palo Alto, Calif.) in order to obtain cDNA for bovine and human EN-RAGE according to the manufacturer's instructions. The sequence encoding bovine cDNA for EN-RAGE is #AS 011757 (Genbank).

3. Protein Expression

The cDNA encoding EN-RAGE was placed into a baculovirus expression system and expressed in Spodoptera frugiperda 9 (Sf9) cells (Invitrogen, Carlsbad, Calif.).

EN-RAGE was purified from cellular pellets by sequential chromatography onto heparin and hydroxylapatite columns (Amersham Pharmacia, Piscataway, N.J.) and eluted with increasing concentrations of NaCl. Purified EN-RAGE, a single band on Coomassie-stained gels, Mr ≈12 kDa, was devoid of endotoxin prior to experiments by chromatography onto Detox-igel columns (Pierce, Arlington Heights, Ill.). Absence of endotoxin was documented using a kit from Sigma (St. Louis, Mo.) (limulus amebocyte assay). Where indicated, purified S100B from human brain (Calbiochem-Novabiochem Corp., San Diego, Calif.) was employed.

4. Immunoblotting

In Vitro Studies Human peripheral blood-derived mononuclear cells were isolated from normal volunteers by using Histopaque 1077 (Sigma) and Jurkat E6 cells were obtained form the American Type Tissue Corporation (Rockville, Md.). Where indicated, cells were stimulated with PMA (10 ng/ml), ionomycin (100 ng/ml), or TNF-a (Genzyme, Cambridge, Mass.) for 12 hrs. Cells ($1 \times 10^7$) were sonicated (Sonifer 250, Branson, Danbury, Conn.) in PBS containing protease inhibitor mixture (Boehringer Mannheim, Indianapolis, Ind.), centrifuged for 30 mins at 14,000 rpm at 4° C. Protein concentration of supernatant was measured using Bio-Rad protein assay (Hercules, Calif.). To each lane of tris-glycine gels (Novex, San Diego, Calif.), 7 μg of protein was added; gels were then transferred to nitrocellulose membranes (Bio-Rad) and immunoblotting performed using polyclonal rabbit monospecific anti-EN-RAGE IgG prepared against full-length recombinant bovine EN-RAGE. Goat anti-rabbit IgG labelled with horseradish peroxidase (Sigma) and ECL system (Amersham-Pharmacia) were employed to indicate sites of primary antibody binding.

In vivo studies LPS (Sigma) (30 μg/g body weight) was injected intraperitoneally into CF-1 mice. Where indicated, certain mice were pretreated with murine sRAGE (100 μg) 12 hrs and 1 hr prior to LPS injection. Mice were sacrificed at the indicated time points and serum (0.015 ml) subjected to electrophoresis using tris-glycine gels (14%; Novex) and. immunoblotting performed as above. In both cases, densitometry was performed using ImageQuant, Molecular Dynamics (Foster City, Calif.).

5. Radioligand Binding Assays

Purified EN-RAGE was radiolabelled using $^{125}$-I and Iodobeads (Pierce) to a specific -activity of approximately 5,000 cpm/ng. Radioligand binding assays were performed in 96-well dishes to which had been adsorbed either purified human RAGE (5 μg/well) or bovine aortic endothelial cells. In the former case, after adsorption of human soluble RAGE to the plastic dish in carbonate/bicarbonate buffer (pH 9.3) overnight, wells were then washed with PBS containing Tween 20 (0.05%). Unoccupied binding sites on the plastic wells were blocked by incubation with PBS containing calcium/magnesium and bovine serum albumin (1%) for two hours at 37° C. After aspiration of the wells, a radioligand binding assay was performed in the presence of the indicated concentration of radiolabelled EN-RAGE ± an 50-fold molar excess of unlabelled EN-RAGE in PBS containing calcium/magnesium and BSA, 0.2%, for 3 hrs at 37° C. At the end of that time, wells were washed rapidly with washing buffer as above; elution of bound material was performed in a solution containing heparin, 1 mg/ml. Solution was then aspirated from the wells and counted in a gamma counter (LKB, Gaithersburg, Md.). In cell binding assays, bovine aortic endothelial cells (SAEC) were plated onto 96-well tissue culture plates previously coated with collagen I (Biocoat; Becton Dickinson, Bedford Mass.). Upon achieving confluence, cells were washed with PBS and radioligand binding assay performed as above. Equilibrium binding data were analyzed according to the equation of Klotz and Hunston (Klotz and Hunston, 1984): $B = nKA/1+KA$, where B=specifically bound ligand (total binding, wells incubated with tracer alone, minus nonspecific binding, wells incubated with tracer in the presence of excess unlabelled material), n=sites/cell, K=the dissociation constant, and A=free ligand concentration) using nonlinear least-squares analysis (Prism; San Diego, Calif.). Where indicated, pretreatment with either antibodies, or soluble RAGE, was performed.

6. Cellular Activation Studies

Endothelial cells Human umbilical vein endothelial cells (HUVEC) were isolated, characterized and maintained as previously described (Schmidt et al., 1995). Cells were cultured in serum-free RPMI 1640 without endothelial cell growth factor for 24 hrs and then stimulated with the indicated concentrations of EN-RAGE or other stimuli. Where indicated, cells were pretreated with rabbit anti-human RAGE IgG, nonimmune rabbit IgG; in certain cases, EN-RAGE was pretreated with the indicated concentration of sRAGE for 2 hrs prior to stimulation with EN-RAGE. After eight hrs stimulation with EN-RAGE, cells were fixed with paraformaldehyde (2%) for 30 mins, washed twice with PBS, treated with PBS containing non-fat dry milk (5%) and BSA (2.5%) to block nonspecific binding sites on the cell surface. Cell surface ELISA employing anti-VCAM-1 IgG (Santa Cruz Biotechnologies, Santa Cruz, Calif.) was performed as previously described (Schmidt et al., 1995b). Assessment of functional VCAM-1 activity was determined using $^{51}$Cr-labelled Molt-4 cells (ATCC) as previously described (Schmidt et al., 1995b). Activation of NF-kB was assessed using nuclear extracts from HUVEC prepared as previously described (Schreiber et al., 1998). 10 μg nuclear extract were loaded onto RAGE gels and EMSA performed using $^{32}$P-labelled probe for NF-kB from the VCAM-1 promoter (Neish et al., 1992). Supershift assays were performed by preincubating nonimmune anti-p50, anti-p65 or both IgG (Santa Cruz) with nuclear extract for 45 mins at room temperature prior to addition of radiolabelled oligonucleotide probe.

7. Peripheral Blood Mononuclear Cells (PBMC), Mononuclear Phagocytes (MPs) and Jurkat Cells Chemotaxis Assays Chemotaxis assays were performed as previously described (Schmidt et al., 1993) in 48-well microchemotaxis chambers (Neuro-Probe, Bethesda, Md.) containing a polycarbonate membrane (8 μm; Nucleopore, Pleasanton, Calif.). The lower chamber contained the chemotactic stimulus as indicated. N-formyl-met-leu-phe (Sigma) was employed as positive control. Molt-4 cells (which bear cell surface RAGE) were added to the upper chamber ($10^4$ cells/well). After incubation for 4 hrs at 37° C., nonmigrating cells on the upper surface of the membrane were gently scraped and removed, the membrane was then fixed in methanol (100%) and cells that had migrated through the membrane were stained with Giemsa (Sigma) and counted. Cells in nine high-powered fields were counted and mean±standard error of the mean reported. Each experiment was repeated twice; in each case, six replicates per condition were employed.

Mitogenic assays In in vitro studies, PBMC were isolated from whole blood using a ficoll gradient (Histopaque 1077; Sigma) and suspended in RPMI containing FBS (10%) at a concentration of $1 \times 10^6$ cells/ml. Cells were seeded in 96-well tissue culture wells and treated as indicated with En-RAGE for 12 hrs prior to stimulation with PHA-P (Sigma) for 12 hrs. Wells were then pulsed with ³H-thymidine (1 μCi/well) (New England Nuclear, Boston, Mass.) and incubated for an additional 18 hrs prior to harvesting and processing for liquid scintillation counting using an LK betaplate (Wallac, Inc., Gaithersburg, Md.). In in vivo studies, mouse splenocytes (CF-1 strain) were obtaining from spleen tissue of mice subjected to DTH studies as described below and isolated using Histopaque 1077. Splenocytes ($5 \times 10^5$ per well; 96 well tissue culture plates) in RPMI containing FBS (10%) were stimulated with PMA (0.5 μg/ml) for 18 hrs and proliferation rate performed as above in in vitro studies using tritiated thymidine. All experiments were performed with triplicate determinations.

Assessment of Cytokine Levels BV2 cells (Yan et al., 1997), which bear cell surface RAGE, or Jurkat E6 cells (ATCC) were incubated as indicated with EN-RAGE for the indicated times. In certain experiments, cells were preincubated with anti-RAGE F(ab')$_2$ prior to stimulation with EN-RAGE. In other cases, EN-RAGE was preincubated with sRAGE prior to stimulation. ELISA for TNF-a, IL-1β or IL-2 was performed using kits from R&D Systems (Minneapolis, Minn.). Where indicated, cells were transfected with a construct encoding human RAGE in which the cytosolic domain (tail) was deleted employing superfect (Qiagen, Valencia, Calif.) (1 μg DNA/ml medium); pcDNA3 (Invitrogen) was employed as vector. Stimulation experiments were performed 48 hrs after transfection.

Infusion studies. BAlb/c mice (Charles River), approximately 6 weeks of age, were injected intravenously via the tail vein with EN-RAGE (30 μg), BSA (30 μg) or LPS (500 μg). Twelve hrs later, lungs were rapidly harvested and homogenized in tris-buffered saline containing protease inhibitor (Boehringer Mannheim) and subjected to centrifugation at 8,000 rpm for 10 mins. The supernatant was then centrifuged for one hr at 4° C. at 40,000 rpm. The pellet was the dissolved in TBS containing protease inhibitors and octyl-β-glucoside (2%) for 4 hrs at 4° C. The suspension was then subjected to centrifugation for 10 mins at 14,000 and supernatant assessed for protein concentration (Bio-Rad). Immunoblotting was performed after electrophoresis of 30 μg protein/lane and transfer of gel components to nitrocellulose. Anti-VCAM-1 IgG was obtained from Santz Cruz Biotechnologies and visualization of bands accomplished with the ECL system (Amersham-Pharmacia).

8. Model of Delayed Hypersensitivity

Female CF-1 mice, 6 weeks of age, were sensitized by subcutaneous injection over the left inguinal lymph node of an emulsion (0.1 ml) containing methylated BSA (mBSA; 25 mg/ml; Sigma), NaCl (0.9%), dextran ($5-40 \times 10^6$ MW; 50 mg/ml; Sigma) and Freund's incomplete adjuvant (50%; ICN Biomedical; Aurora, Ohio). Three weeks later, the left plantar hind paw was injected subcutaneously with mBSA (0.4 mg/ml; 0.050 ml). Where indicated, mice were pretreated by intraperitoneal injection with sRAGE (indicated dose), mouse serum albumin (Sigma), immune or nonimmune F(ab')$_2$ fragments (prepared using a kit from Pierce, Arlington Heights, Ill.) 24 and 12 hrs prior to, and 6 and 12 hrs after local challenge with mBSA. 24 hrs after injection of foot pad with mBSA, clinical score of foot pad as described above was performed by two blinded investigators; mice were then humanely sacrificed and feet fixed in formalin (10%) or frozen for further analysis. Histologic score was performed on sections of foot stained with hematoxylin and eosin (Sigma) by two blinded investigators. Electrophoretic mobility shift assay was performed employing 10 μg foot pad nuclear extract added per lane as above. RT-PCR was performed using commercially-available primers (Clontech) for IL-2 (expected size; 413 base pairs), TNF-a (expected size; 310 base pairs) and β-actin (expected size; 540 base pairs). In certain mice, upon sacrifice, spleen was retrieved and splenocytes prepared by separation with Histopaque 1077 (Sigma). Into the wells of 96-well tissue culture plates, $5 \times 10^4$ cells were placed and stimulation performed with PMA, 0.5 μg/ml, for 16 hrs. At the end of that time, tritiated thymidine was added for an additional 18 hrs. Cells were then retrieved and counted in a beta counter.

9. Model of Chronic Colitis in IL-10 Null Mice

IL-10 null mice in the C57BL/6 background (Jackson Laboratories, Bar Harbor, Me.) were born and bred into pathogen-free conditions. At the age of 3 weeks, mice were moved into standard conventional housing with free access to chow and water. One week after placement in standard conditions, mice were treated once daily by intraperitoneal injection for six weeks with either MSA (100 μg/day) or sRAGE (100 μg/day). At the end of that time, mice were deeply anesthetized; plasma removed and then rectosigmoid colon removed for histologic analysis (hematoxylin and eosin) or preparation of nuclear extract as described above. Hematoxylin and eosin-stained sections of rectosigmoid were evaluated blindly by one of the investigators. Plasma was assessed for levels of TNF-a (R&D systems) and EMSA for NF-kB performed on nuclear extracts.

Results

1. Characterization of the ≈12 kDa RAGE-Binding Protein

We previously speculated that such a receptor in the immunoglobulin superfamily might engage ligands beyond AGEs. Upon preparation of detergent extract of bovine lung, and chromatography of the material onto sequential columns, including at the last step, a resin of Affi-gel to which had been adsorbed RAGE, two polypeptides were eluted which bore RAGE-binding activity in radioligand binding assays. The first, an ≈23 kDa polypeptide, was identified as amphoterin (Hori et al., 1995). The second, an ≈12 kDa polypeptide, was subjected to amino acid sequence analysis both at the amino-terminus, and internally, after digestion with the endopeptidase, Lys-C (Table 2). The sequence of this polypeptide, initially termed "p12," revealed that it bore its closest and striking homology to a polypeptide known as bovine calcium-binding protein in amniotic fluid-1 (CAAF-1) (Hitomi et al., 1996) or bovine corneal antigen/calgranulin C (Gottsch et al., 1997), recently classified as S100A12 (Ilg et al., 1996). This polypeptide was subsequently called EN-RAGE, Extracellular Novel RAGE binding protein. The sequence of EN-RAGE differed from that of bovine corneal antigen by two amino acids. At position #30, EN-RAGE was composed of a tyrosine (Y), while bovine corneal antigen was composed of an arginine (R). At position #36, EN-RAGE was composed of a glycine (G), while bovine corneal antigen was composed of an isoleucine (I) (Table 2). Molecular cloning studies revealed that EN-RAGE was a member of the calgranulin/S100 family of proinflammatory cytokines. Two cDNA clones obtained from a bovine lung library encoded polypeptides identical to bovine corneal antigen based on deduced amino acid sequence; with an arginine at position #30 and an isoleucine at position #36. Based on these date, we cannot exclude the possibility that we did not isolate specific clones encoding the precise sequence of EN-RAGE. Molecular cloning employing a human lung library produced one clone; deduced amino acid sequence of the cDNA revealed that the human counterpart of EN-RAGE was likely to be human calgranulin C (or human corneal antigen/S100A12). (Gottsch and Liu, 1998; Ilg et al., 1996; Yamamura et al., 1996) The deduced amino acid sequence of the polypeptide revealed that the human counterpart was highly homologous to bovine corneal antigen (>77%).

Figure 6A:
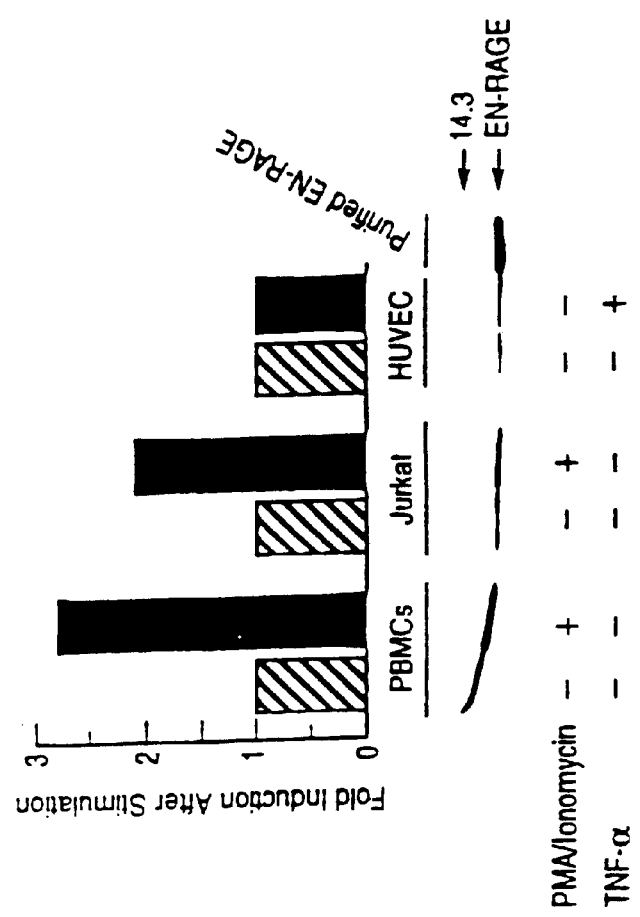

Indeed, p12 is a member of the S100/calgranulin superfamily (Dell'Angelica et al., 1994; Ilg et al., 1996; Wicki et al., 1996; Gottsch et al., 1997; Gottsch and Liu, 1998). We thus retained the name EN-RAGE because a novel property of this and other such family members is their interaction with RAGE, which has important implications for function of these polypeptides as described below.

nate revealed increased generation of EN-RAGE, 2.8-fold and 2.1-fold, respectively (FIG. 6A). In contrast, upon stimulation of cultured human umbilical vein endothelial cells (HUVEC) with a prototypic stimulus, tumor necrosis factor-a, modulation of EN-RAGE expression did not ensue (FIG. 6A). Similarly, exposure of HUVEC to PMA/ionomycin did not increase expression of EN-RAGE (data

TABLE 2

Amino acid sequence analysis of p12 (SEQ ID NO:2), later termed "EN-RAGE", and comparison with homologous polypeptides bovine corneal antigen (SEQ ID NO:3) and bovine CAAF1 (SEQ ID NO:4) and P12 CNBR (SEQ ID NO:5). The latter sequences were obtained from Gottsch et al, 1997. A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp and Y, tyr. X is an amino acid residue not identified at that position.

```
                    1                   10                  20
P12                 T K L E D H L E G I I N I G H Q Y S V R V G H F
N-TERM                              30
                    D T L N K Y

P12 CNBR

B-COAg              T K L E D H L E G I I N I F H Q Y S V R V G H F
                    D T L N K R

B-CAAF1             T K L E D H L E G I I N I F H Q Y S V R V G H F
                    D T L N K R 31                  40                  50
P12                 E L K Q L G T K E L P K T L Q N X K D Q
N-TERM

P12 CNBR

B-COAg              E L K Q L I T K E L P K T L Q N T K D Q P T I D
                    K I F Q D L

B-CAAF1             E L K Q L I T K E L P K T L Q N T K D Q P T I D
                    K I F Q D L 61                  70                  80
P12
N-TERM

P12 CNBR                        D G A V S F E E F V V L V S R V L K

B-COAg              D A D K D G A V S F E E F V V L V S R V L K T A
                    H I D I H K

B-CAAF1             D A D K D G A V S F E E F V V L V S R V L K T A
                    H I D I H K
```

2. Expression of EN-RAGE is Enhanced in Stimulated Inflammatory Cells

The S100/calgranulin family of molecules has been extensively associated with a broad range of inflammatory disorders, especially those of chronic nature. Since these polypeptides are known to be released from inflammatory cells such as polymorphonuclear leukocytes and peripheral blood derived mononuclear phagocytes, it has long been speculated that they may play a role in development of the inflammatory phenotype, such as by stimulating macrophage migration and activation. We thus tested the concept that ligation of RAGE by EN-RAGE would activate pro-inflammatory cell signalling pathways, thereby leading to modulation of gene expression in a manner linked to inflammation.

When peripheral blood mononuclear cells (PBMC) or Jurkat cells, an immortalized T cell line, were stimulated with PMA/ionomycin, immunoblotting of cellular homogenot shown). Thus, typical of members of the S100/calgranulin family, expression of EN-RAGE may be modulated in stimulated inflammatory cells.

Figure 6B:
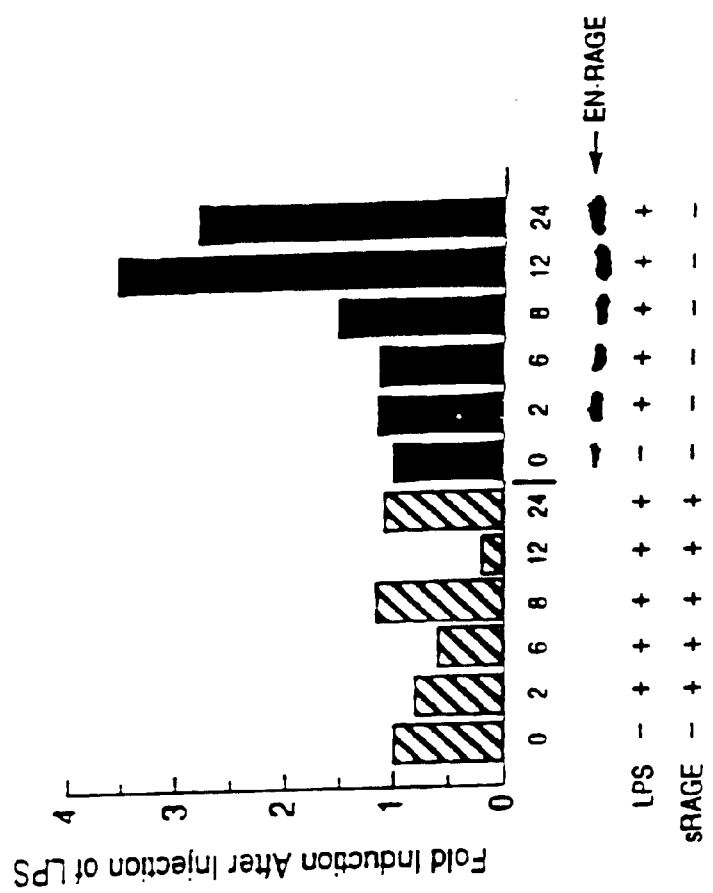

To determine if EN-RAGE is released in an inflammatory environment in vivo, lipopolysaccharide (LPS) was infused intravenously into mice. A time-dependent increase in release of EN-RAGE into plasma was noted (FIG. 6B). Maximal release of EN-RAGE was observed 12 hrs after injection; an ≈3.6-fold increase in EN-RAGE by immunoblotting was demonstrated at that time (FIG. 6B). Consistent with the possibility that soluble RAGE, the extracellular ligand-binding portion of RAGE, might engage EN-RAGE in plasma, thereby facilitating its clearance and removal, concomitant administration of sRAGE (which does not bind LPS) and LPS resulted in no detectable increase in plasma EN-RAGE by immunoblotting (FIG. 6B), even at 12 hrs after injection of LPS (FIG. 6B).

Figure 6C:
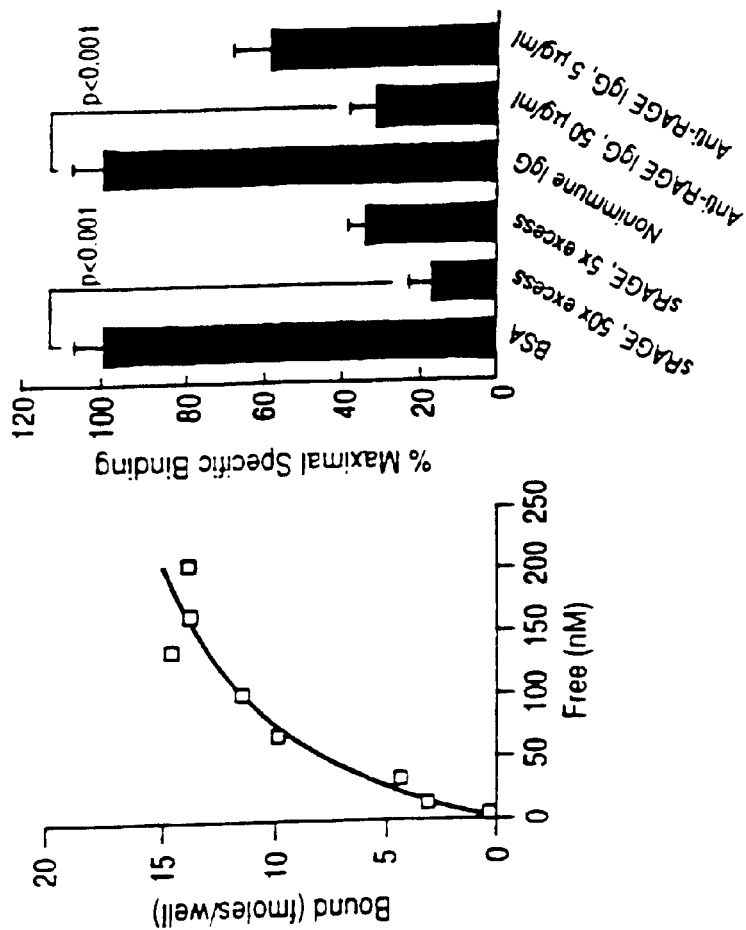

These data suggested that EN-RAGE bound RAGE. In radioligand binding assays, $^{125}$-I EN-RAGE bound immobilized RAGE on plastic wells in a dose-dependent manner, with $K_d \approx 91 \pm 29$ nM and capacity $\approx 21 \pm 2.9$ fmoles/well (FIG. 6C) Upon incubation of radiolabelled EN-RAGE with excess unlabelled sRAGE, binding to immobilized RAGE was significantly attenuated (FIG. 6C, inset). Specific binding of radiolabelled EN-RAGE to RAGE was diminished 82.5% in the presence of a 50-fold molar excess of unlabelled RAGE. In contrast, incubation with excess unlabelled bovine serum albumin (BSA) was without effect (FIG. 6C). Furthermore, preincubation of immobilized RAGE with anti-RAGE IgG significantly inhibited binding of radiolabelled EN-RAGE to immobilized RAGE (FIG. 6C, inset). In the presence of anti-RAGE IgG, 50 µg/ml, binding was inhibited by 67.9%. In contrast, preincubation with nonimmune IgG was without effect (FIG. 6C, inset). Importantly, preincubation with excess human S100B also significantly suppressed binding of EN-RAGE to RAGE, suggesting that a range of S100/calgranulin polypeptides bind RAGE.

Figure 6D:
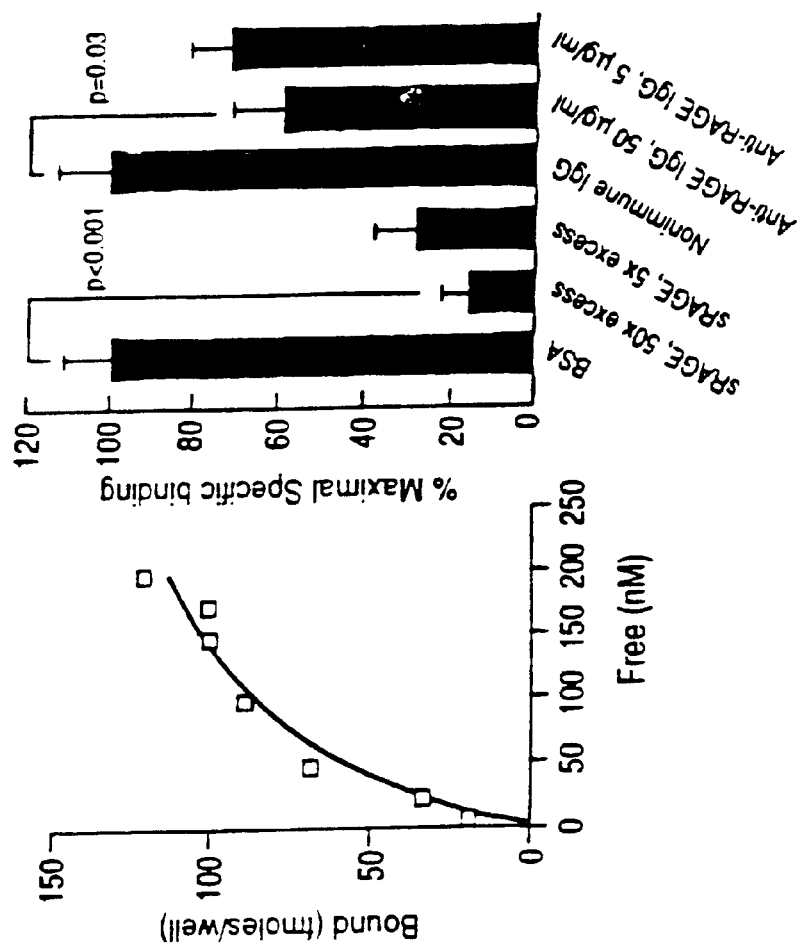

It was critical, however, to determine if EN-RAGE might engage RAGE on the surface of cells involved in the inflammatory response. To test this, we performed radioligand binding assays in cultured bovine aortic endothelial cells (BAEC). Consistent with our previous studies, $^{125}$-I-EN-RAGE bound BAEC RAGE in a dose-dependent manner, with $K_d \approx 90.3 \pm 34$ nM and capacity $\approx 163 \pm 26.2$ fmoles/well (FIG. 6D), similar to that observed with other ligands of RAGE, such as AGEs (Schmidt et al., 1992) and amphoterin (Hori et al., 1995). Specific binding of radiolabelled EN-RAGE to BAEC RAGE was diminished 84.3% in the presence of a 50-fold molar excess of unlabelled RAGE. In contrast, incubation with excess unlabelled BSA was without effect (FIG. 6D, inset). Binding of radiolabelled EN-RAGE to RAGE was inhibited 41% upon preincubation of BAEC with anti-RAGE IgG, 50 µg/ml, but only 28.7% in the presence of anti-RAGE IgG, 5 µg/ml. In contrast, nonimmune IgG was without effect (FIG. 6D, inset). Similar results were observed in macrophage-like cultured BV2 cells (not shown).

These data indicated that EN-RAGE bound RAGE in a specific manner and led us to hypothesize that ligation of RAGE by EN-RAGE might trigger cellular activation.

Figure 7A:
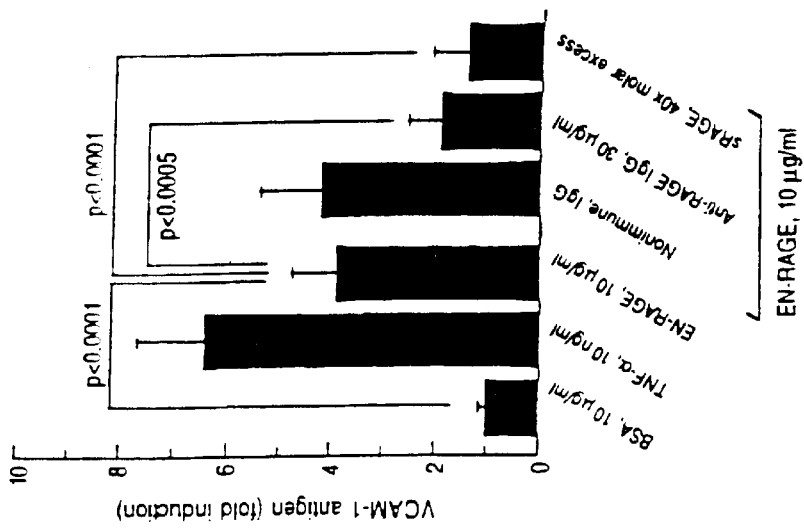

3. Ligation of RAGE by EN-RAGE and EN-RAGE-Like Molecules Activates Cells Central to the Inflammatory Response Endothelial Cells Since activation of endothelium is a central component of the inflammatory response, we first tested the ability of EN-RAGE to activate EC RAGE. Consistent with this hypothesis, incubation of EN-RAGE with cultured human umbilical vein endothelial cells (HUVEC) resulted in increased cell surface expression of Vascular Cell Adhesion Molecule-1, an important means by which mononuclear cells bearing VLA-4 may be targetted to stimulated endothelium (Li et al., 1993; Richardson et al., 1994) (FIG. 7A). That this was largely mediated by RAGE was evident upon experiments in which access to RAGE was inhibited. Preincubation of EN-RAGE with a 40-fold molar excess of sRAGE significantly attenuated expression of VCAM-1 as did preincubation of the cells with anti-RAGE IgG (FIG. 7A). In contrast, preincubation with nonimmune IgG resulted in no change in the extent of cell surface VCAM-1 expression after treatment with EN-RAGE (FIG. 7A). Consistent with the observation that ligation of RAGE by EN-RAGE resulted in increased cell surface expression of VCAM-1, increased binding of VLA-4-bearing Molt cells was noted to EN-RAGE stimulated endothelium. The ability of EN-RAGE to enhance Molt-4 binding to HUVEC was dose-dependent (FIG. 7B, left panel).

Figure 7B:
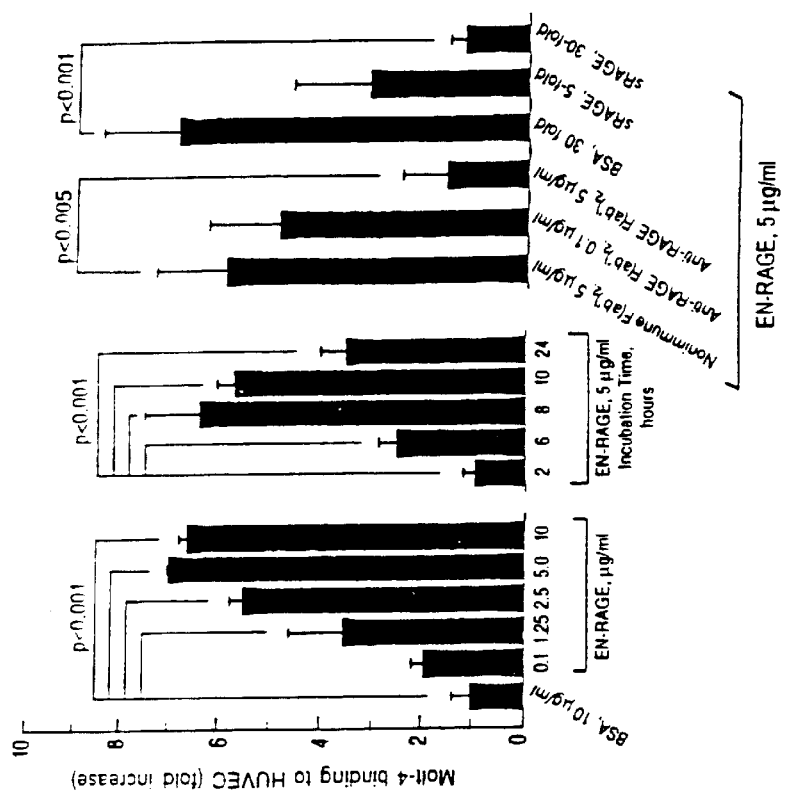

The effects of EN-RAGE were time-dependent; with maximal increase in Molt-4 binding observed after 8 hrs incubation (FIG. 7B, middle panel). Consistent with our previous findings, increased Molt-4 binding was due to interaction of EN-RAGE with cellular RAGE. Preincubation of HUVEC with anti-RAGE F(ab')$_2$, 5 µg/ml, significantly attenuated Molt-4 binding to EN-RAGE-treated cells. In contrast, both anti-RAGE F(ab')$_2$, 0.1 µg/ml and nonimmune F(ab')$_2$ were without effect (FIG. 7B, right panel). Similarly, preincubation of EN-RAGE with a 30-fold molar excess of sRAGE significantly attenuated EN-RAGE-mediated enhancement of Molt-4 binding to HUVEC. In contrast, preincubation of EN-RAGE with either sRAGE (5-fold molar excess) or BSA, 5 µg/ml, were without significant effect (FIG. 7B, right panel)

Figure 7C:
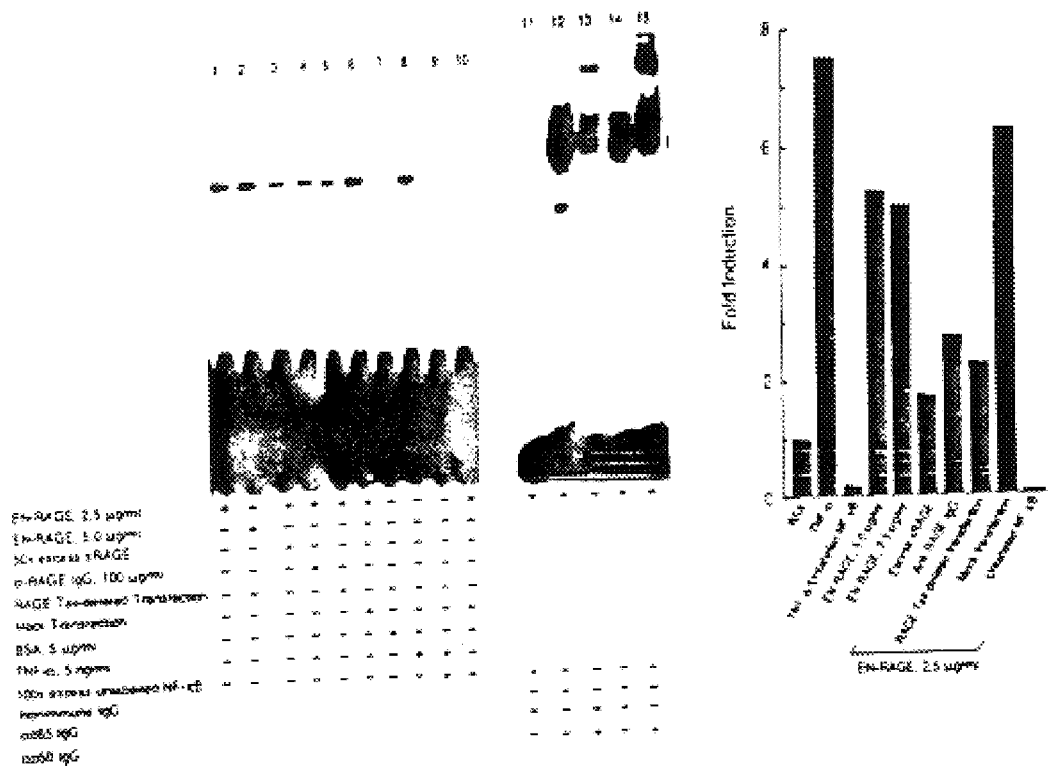
Figure 7G:
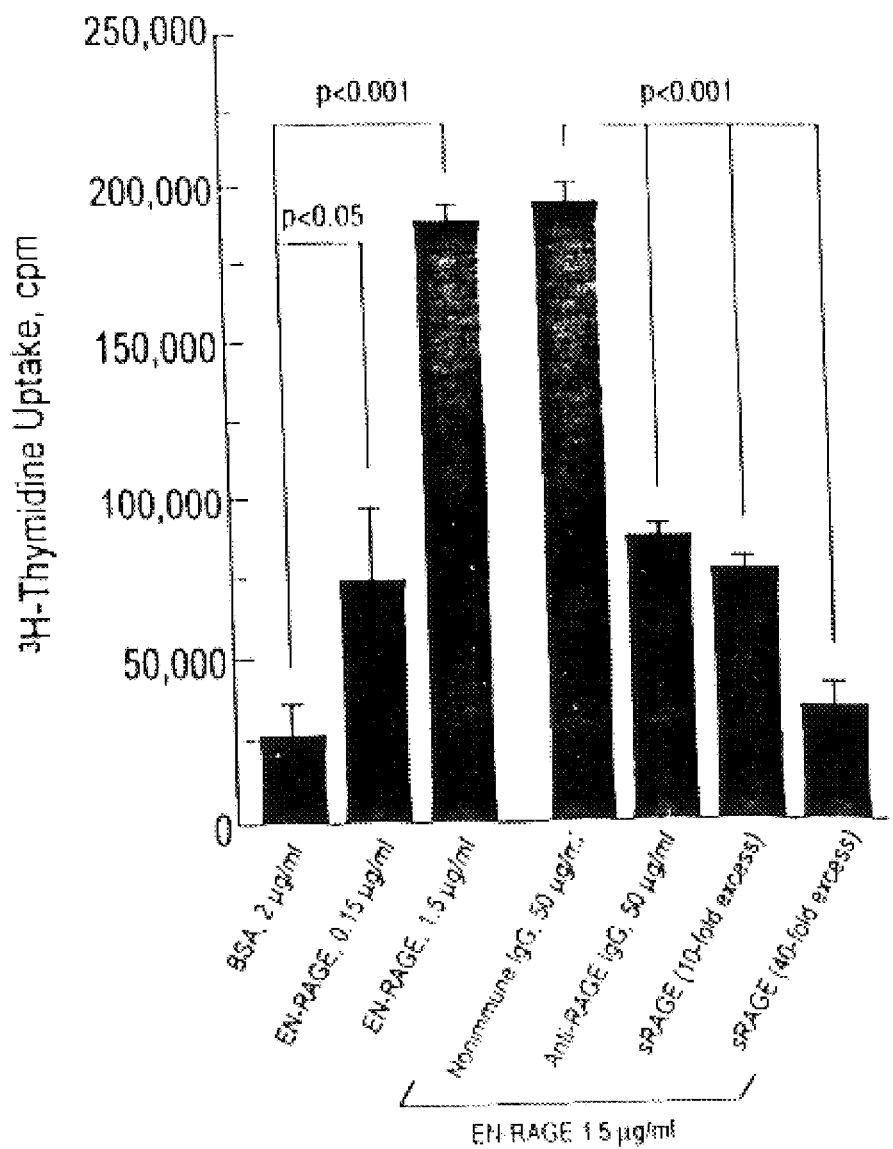

An important means by which increased mRNA for VCAM-1 results is by activation of central transcription factor in the inflammatory response, NF-kB (Neish et al., 1992). In previous studies, we demonstrated that ligation of RAGE by AGEs and amyloid-β peptide resulted in enhanced translocation of NF-KB components into the nucleus, as demonstrated by electrophoretic mobility shift assay (Yan et al., 1994; Yan et al., 1996; Lander et al., 1997). We thus tested whether ligation of EC RAGE by EN-RAGE mediated activation of NF-kB. In electrophoretic mobility shift assay (EMSA) of nuclear extracts prepared from HUVEC, incubation with EN-RAGE (2.5 or 5. 0 µg/ml) resulted in an ≈5-fold increase in nuclear NF-KB by densitometry compared with incubation with BSA (FIG. 7C, lanes 1, 2, and 7, respectively and inset). That this was largely mediated by interaction with RAGE was demonstrated by experiments in which HUVEC were pretreated with anti-RAGE IgG prior to EN-RAGE, in which activation of NF-kB was significantly attenuated (FIG. 7C, lane 4 and inset). Similarly, preincubation of EN-RAGE with excess sRAGE (50-fold) resulted in diminished activation of NF-KB (FIG. 7C, lane 3 and inset). Supershift assays employing both anti-p50 and anti-p65 IgG demonstrated that the NF-kB complex activated upon ligation of RAGE by EN-RAGE was composed of both p50 and p65 (FIG. 7C, lanes 13, 14, and 15). In contrast, preincubation of the nuclear extract with nonimmune IgG did not result in band shift (FIG. 7C, lane 12). To test the concept that the cytosolic domain of RAGE was critical for activation of signalling pathways proximal and essential to activation of NF-kB, transient transfection of HUVEC was performed with a construct encoding human RAGE in which the cytosolic domain was deleted. Consistent with an important role for the cytosolic domain in mediating cell signalling, EN-RAGE-stimulated activation of NF-kB was markedly suppressed in RAGE cytosolic tail deleted transfectants (FIG. 7C, lane 5 and inset) compared with those transfected with vector alone (FIG. 7C, lane 6 and inset).

Taken together, these data suggested that EN-RAGE-RAGE interaction in endothelial cells activated an important transcription factor, NF-kB, involved in the inflammatory response, thereby suggesting a central means by which this interaction might impart proinflammatory perturbation.

Mononuclear Phagocytes

In addition to endothelial cells, mononuclear phagocytes (MPs) are critically important in mediating immune/inflammatory events. We hypothesized that EN-RAGE released from cells recruited to sites of injury might be further important in amplifying the inflammatory response. We thus tested the ability of EN-RAGE to stimulate migration of MP-like cells. In modified chemotaxis chambers EN-RAGE placed in the lower chamber mediated chemotaxis of Molt-4 cells (which bear cell surface RAGE) placed in the upper chamber in a dose-dependent manner (FIG. 7D, left panel, lines 2, 3, 4 and 5). In contrast, placement of BSA in the lower chamber was without significant effect (FIG. 7D, line 1). That this represented true chemotaxis was suggested by experiments in which EN-RAGE was placed in both upper and lower chamber. When Molt-4 cells were added, no significant migration to the lower chamber occurred FIG. 7D, left panel, line 6). To test the concept that RAGE on the surface of MP cells was a principal means by which EN-RAGE stimulated migration, EN-RAGE was preincubated with excess sRAGE; a significant attenuation of Molt-4 migration to the lower chamber resulted (FIG. 7D, right panel, lines 2 and 3) compared with preincubation with BSA (FIG. 7D, right panel, line 1). Furthermore, when Molt-4 cells were preincubated with anti-RAGE F(ab')$_2$, a significant decrease in EN-RAGE-mediated Molt-4 migration occurred (FIG. 7D, right panel, lines 5 and 6). In contrast, preincubation with nonimmune F(ab')$_2$ was without effect (FIG. 7D, right panel, line 4).

We sought to delineate if interaction of EN-RAGE with MP RAGE resulted in enhanced generation of mediators such as IL-1β and TNF-a, cytokines critically linked to cellular activation and inflammation. Incubation of mock-transfected (vector alone) cultured macrophage-Like BV2 cells with EN-RAGE resulted in a significant elaboration of IL-1β into cellular supernatant in a dose-dependent manner (FIG. 7E, left panel, filled in bars). That intact RAGE intracellular signalling pathways were essential was demonstrated by experiments in which human RAGE-tail deletion construct was transiently transfected into BV2 cells; complete suppression of EN-RAGE mediated elaboration of IL-1β into the supernatant resulted, consistent with a "dominant negative" effect (FIG. 7E, left panel, hatched bars). Similar results were observed upon examination of TNF-a; EN-RAGE-RAGE interaction resulted in significantly increased expression of TNF-a into cellular supernatants in a dose-dependent manner (FIG. 7E, right panel, filled in bars). However, upon transient transfection with the RAGE-tail deletion construct, elaboration of TNF-a into BV2 supernatant was abolished (FIG. 7E, right-panel, hatched bars) A central means by which modulation of cytokine expression in MPs eventuated was by activation of NF-kB. Similar to results obtained with cultured HUVEC, EMSA of nuclear extracts prepared from EN-RAGE-stimulated BV-2 cells revealed activation of NF-kB, a process markedly suppressed in the presence of anti-RAGE F(ab')$_2$, sRAGE, or transfection with tail-deletion construct (data not shown).

Peripheral Blood Mononuclear Cells and Jurkat Cells

Ligation of RAGE by EN-RAGE in Jurkat cells mediates activation. Incubation of peripheral blood-derived mononuclear cells (PBMC) with EN-RAGE primed cells for an exaggerated response when stimulated with PHA-P. Compared with pretreatment with BSA, significant uptake of tritiated thymidine was noted in cells previously incubated with EN-RAGE (FIG. 7F). That this was largely due to interaction of EN-RAGE with PBMC RAGE was demonstrated by studies in which PBMC were incubated with anti-RAGE IgG, or EN-RAGE was preincubated with excess sRAGE; significant attenuation of EN-RAGE-stimulated incorporation of tritiated thymidine ensued (FIG. 7F).

Consistent with evidence for generalized PBMC activation, incubation of Jurkat cells (which bear cell surface RAGE) with EN-RAGE resulted in increased elaboration of Il-2 into the supernatant medium in a RAGE-dependent manner (FIG. 2G).

Taken together, these studies demonstrate that engagement of RAGE on the surface of cells critical to propagation of the inflammatory response, such as endothelial cells, MPs and lymphocytes, resulted in activation of these cells, in a manner linked to stimulation of migration, proliferation and generation of cytokine mediators, responses essential for orchestration of the inflammatory phenotype.

Figure 7H:
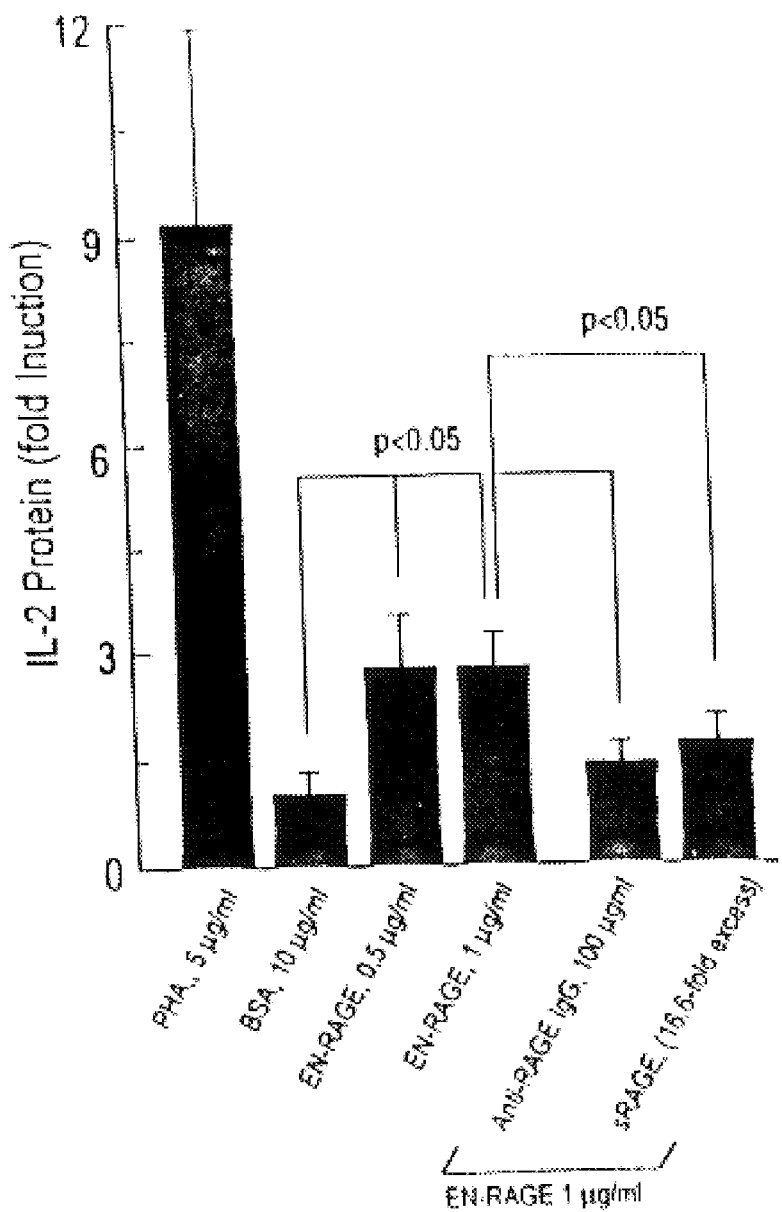

Importantly, we sought to test the range of S100/calgranulin superfamily members that are ligands of RAGE and tested the ability of human S100B to activate ECs. Since activation of NF-kB is an essential precursor to modulation of inflammatory gene expression, we tested this concept by EMSA. When HUVEC were stimulated with human S100B, an ≈13.9-fold increase in nuclear translocation of NF-kB was evident by EMSA (FIG. 7H, lane 2) compared with exposure of cells to BSA (FIG. 7H, lane 1). That these findings were due to activation of RAGE was demonstrated by studies in which either preincubation with anti-RAGE IgG (FIG. 7H, lane 3), or transfection with RAGE tail-deleted construct, markedly attenuated responsiveness to S100B (FIG. 7H, lane 5). In contrast, preincubation with nonimmune IgG (FIG. 7H, lane 4) or mock transfection (FIG. 7H, lane 6) were without effect. These observations indicate that a range of S100/calgranulin polypeptide ligands engage RAGE.

Figure 8A:
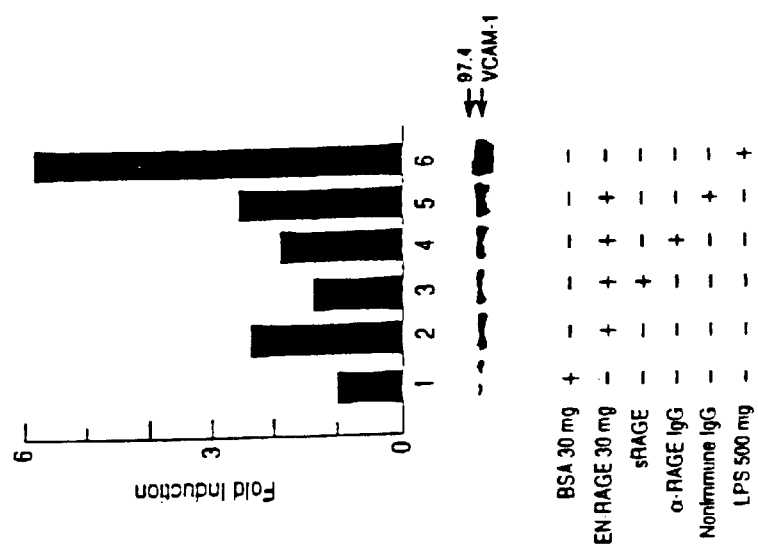
Figure 8B:
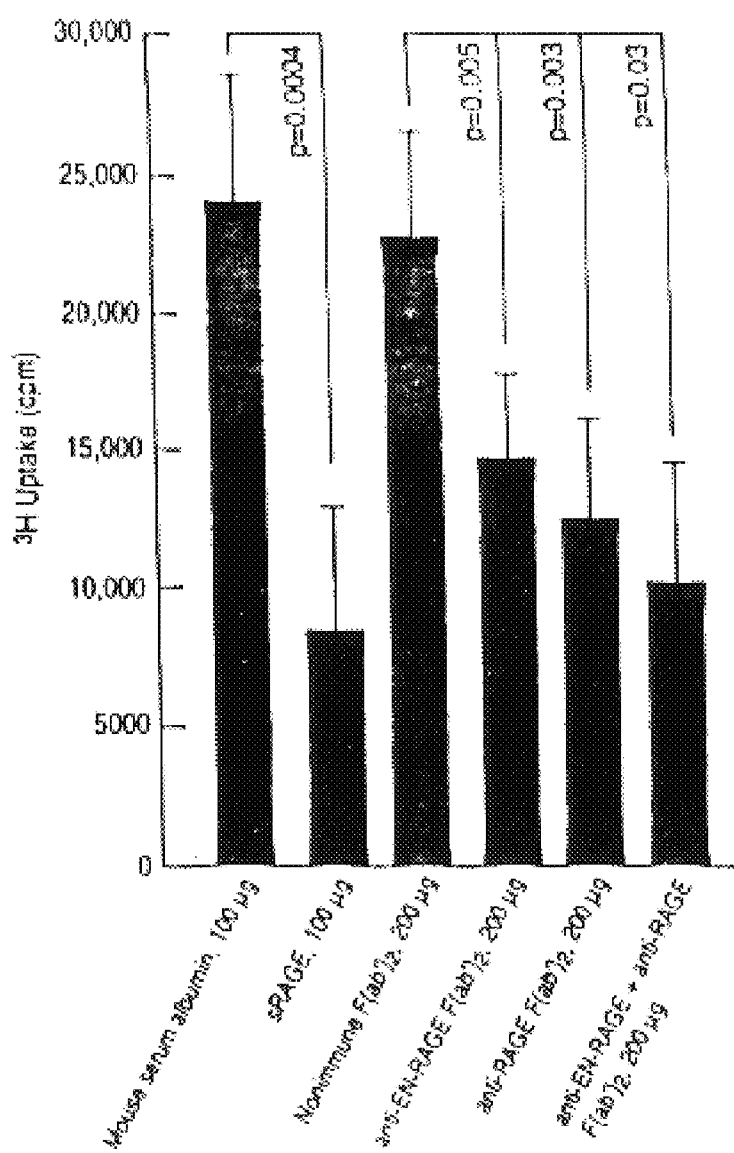

4. Infusion of EN-RAGE Into Mice Stimulates Cellular Activation and Modulation of Gene Expression We sought to extend our findings in in vitro models to determine if EN-RAGE mediated cellular activation and expression of inflammatory mediators in vivo. Although we speculate that in vivo, EN-RAGE is released locally at sites of immune/inflammatory challenge, we tested the concept that infusion of EN-RAGE into immune-competent mice would mediate expression of inflammatory mediators. Consistent with this concept, infusion of EN-RAGE, 30 μg, into CF-1 mice resulted in an μ2.4 increase in expression of VCAM-1 in the lung by immunoblotting compared with infusion of BSA (FIG. 8A, lanes 2 and 1, respectively). That this was largely due to engagement of vascular RAGE was demonstrated by significant attenuation of EN-RAGE-stimulated VCAM-1 expression in the lung in the presence of either sRAGE (FIG. 8A, lane 3) or anti-RAGE IgG (FIG. 8A, lane 4). In contrast, infusion of nonimmune IgG/EN-RAGE was without effect (FIG. 8A, lane 5).

5. Role of EN-RAGE and RAGE in the Inflammatory Response

Acute Inflammation

The critical test of these hypotheses, however, was whether EN-RAGE and RAGE participate in the inflammatory response in in vivo models of inflammation. We first tested this concept in a murine model of delayed-type hypersensitivity (Dunn et al., 1993). In this model, CF-1 mice were sensitized with methylated BSA (mBSA; which does not bind RAGE). mBSA, mixed with an emulsion containing sodium chloride, dextran and incomplete Freund's adjuvant, was injected locally over the lymph nodes of the groin. Twenty-one days later, mBSA or vehicle (phosphate-buffered saline) was injected into the left hind footpad. Our studies indicated that the latter was without effect, and, similarly, injection of mBSA without prior sensitization did not elucidate an inflammatory response (data not shown). In mice both sensitized and challenged with mBSA in the left hind footpad, a significant inflammatory response ensued as measured by inflammation score (FIG. 9A, B, F).

Figure 9A:
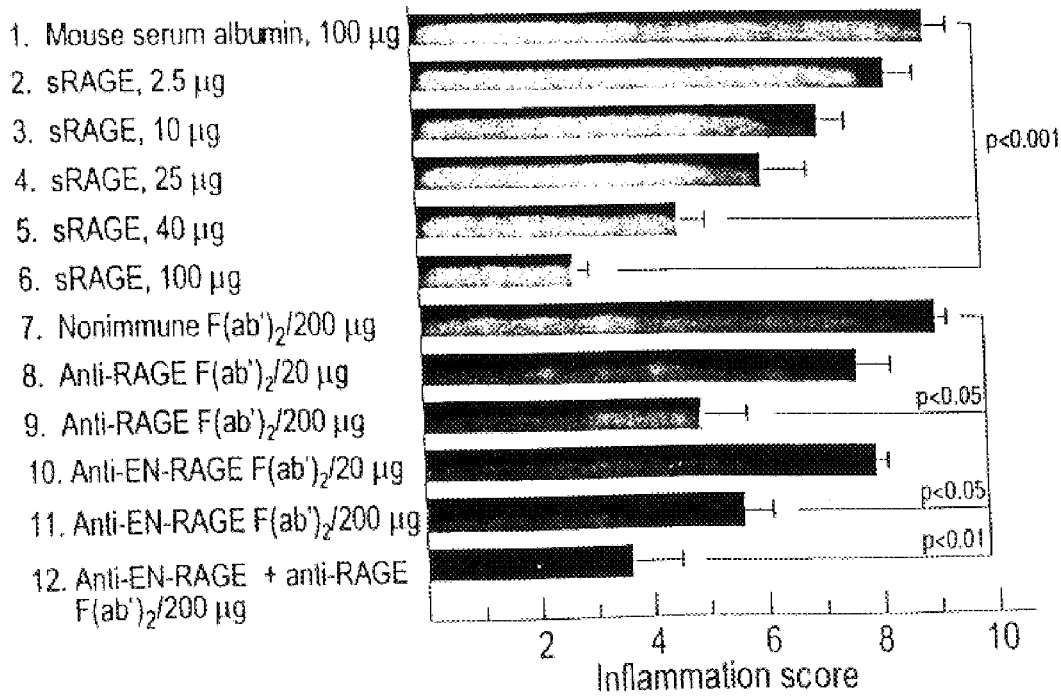

To test the role of blockade of RAGE/EN-RAGE in potentially modulating inflammation in this model, certain sensitized/challenged mice were treated intraperitoneally with vehicle, murine serum albumin (MSA). 24 hrs after injection of mBSA into the footpad, significant evidence of local inflammation was evident (score, 9.0±0.4) (FIG. 9A, line 1; and FIG. 9B). Further, H&E analysis of the affected footpad confirmed a marked influx of inflammatory cells, with granulomata, as well as significant edema (FIG. 9F). In marked contrast, however, injection of murine sRAGE resulted in dose-dependent suppression of inflammation in mBSA-sensitized/challenged mice; upon injection of sRAGE, 100 µg/dose, inflammation score was reduced to 2.7±0.3; $p<0.001$ compared with MSA (FIG. 9A, lines 2-3-4-5 and 6; and FIG. 9C). Consistent with marked suppression of inflammation, examination of the footpad by H&E in sRAGE (100 µg)-treated mice revealed a striking abrogation of inflammatory cell influx into the area (FIG. 9H). We speculate that, at least in part, sRAGE exerts its propitious anti-inflammatory effects by binding up EN-RAGE and inhibiting its engagement and activation of cellular RAGE.

It was thus crucial to determine if blockade of EN-RAGE, employing anti-EN-RAGE F(ab')$_2$ or blockade of access to RAGE itself, employing anti-RAGE F(ab')$_2$, would exert similar beneficial effects, thereby validating an important role for these mediators in the inflammatory cascades triggered by injection of sensitized mice with mBSA. When sensitized/challenged mice were treated with nonimmune F(ab')$_2$, no effect was noted (score, 9.0±0.2). However, in the presence of anti-RAGE F(ab')$_2$(200 µg) or anti-EN-RAGE F(ab')$_2$, significant attenuation of the inflammatory response was evident (FIG. 9A, lines 9 and 11, respectively and FIG. 9E and D, respectively), with inflammation scores 4.9±0.8 and 5.6±0.5, respectively ($p<0.05$ in both cases compared with treatment with nonimmune F(ab')$_2$). Confirming diminished inflammation in the presence of either anti-RAGE F(ab')$_2$ or anti-EN-RAGE F(ab')$_2$, histologic analysis revealed a significant reduction in numbers of inflammatory cells, edema and absence of granulomata (FIG. 9J and I, respectively). Strongly supportive of a critical role for EN-RAGE/RAGE in mediating inflammation, a striking attenuation of inflammation was observed when both anti-EN-RAGE and anti-RAGE F(ab')$_2$ were administered simultaneously (FIG. 9A, line 12); inflammation score was reduced to 3.6±0.9; $p<0.01$ compared with treatment with nonimmune F(ab')$_2$. Indeed, analysis by H&E revealed markedly decreased numbers of inflammatory cells and edema (FIG. 9K).

These data suggested that blockade of EN-RAGE/RAGE substantially quenched cellular activation in this model. Indeed, parallelling evidence of decreased inflammation in mBSA-sensitized/challenged mice to whom sRAGE, anti-RAGE F(ab')$_2$, or anti-RAGE/anti-EN-RAGE F(ab')$_2$ was administered, significant suppression of activation of NF-kB in nuclear extracts prepared from the affected footpads was observed. Compared with contralateral footpad (sensitization with mBSA/absence of local challenge), nuclear extracts from mBSA-injected footpad revealed an ≈6.4-fold increase in activation of NF-KB by EMSA (FIG. 9L, lanes 1 and 2, respectively). In the presence of sRAGE, IP, 100 µg/dose, significant reduction in activation of NF-kB was noted compared with treatment with vehicle, MSA, IP (FIG. 4L, lanes 4 and 2, respectively). Upon treatment with anti-RAGE/anti-EN-RAGE F(ab')$_2$ in mBSA-sensitized/challenged mice, an ≈75% decrease in activation of NF-kB was noted (FIG. 9L, lane 6) compared with treatment with nonimmune F(ab')$_2$(FIG. 9L, lane 7). Taken together, these data strongly suggested that blockade of EN-RAGE/RAGE potently quenched activation of the cell signalling pathway NF-kB.

Figure 9M:
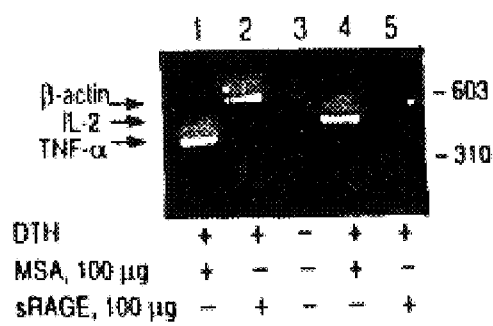

Since an important consequence of ligation of RAGE by EN-RAGE was increased expression of inflammatory mediators, at least in part mediated by activation of NF-kB, we performed RT-PCR from RNA extracted from mBSA-sensitized/challenged mice treated with sRAGE, 100 µg, and found absence of transcripts for either IL-2 or TNF-a (FIG. 9M, lanes 5 and 2, respectively). In contrast, transcripts for IL-2 and TNF-a were evident in footpads from vehicle, MSA-treated mice (FIG. 9M, lanes 4 and 1, respectively).

When splenocytes from mice subjected to DTH were isolated and analyzed ex vivo, diminished mitogenic response in the presence of PMA was noted in those splenocytes retrieved from mice treated with either sRAGE, anti-RAGE F(ab')$_2$ or anti-EN-RAGE F(ab')$_2$ when compared with splenocytes from mice treated with either MSA or nonimmune F(ab')$_2$(FIG. 3B).

Taken together, these data suggest that blockade of EN-RAGE-RAGE interaction in delayed-type hypersensitivity significantly suppressed activation of cell signalling pathways, modulation of gene expression and the inflammatory phenotype.

Chronic Inflammation

Figure 10A:
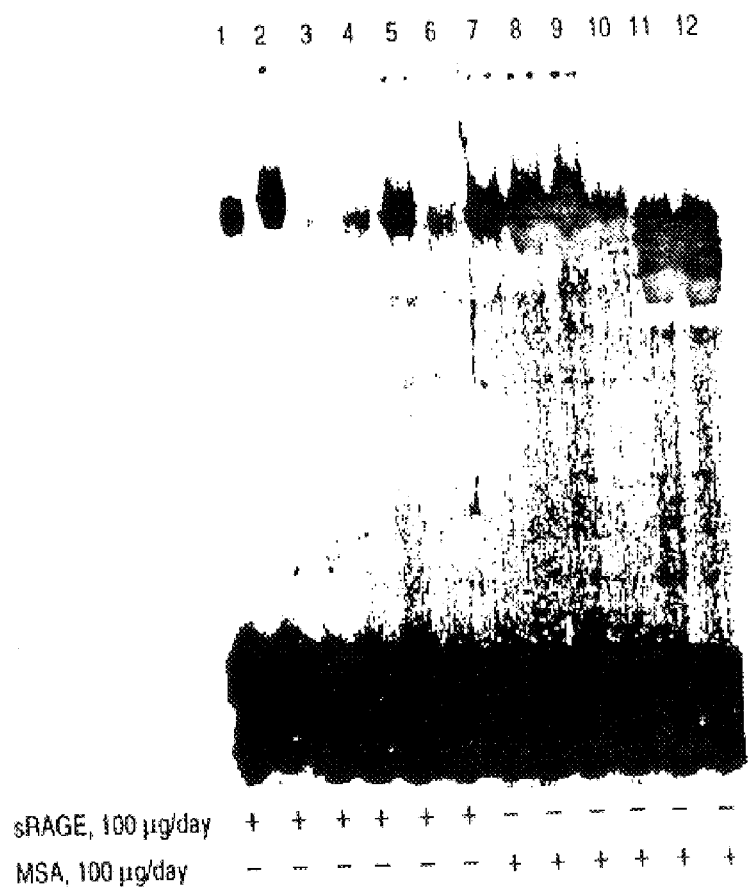
Figure 10B:
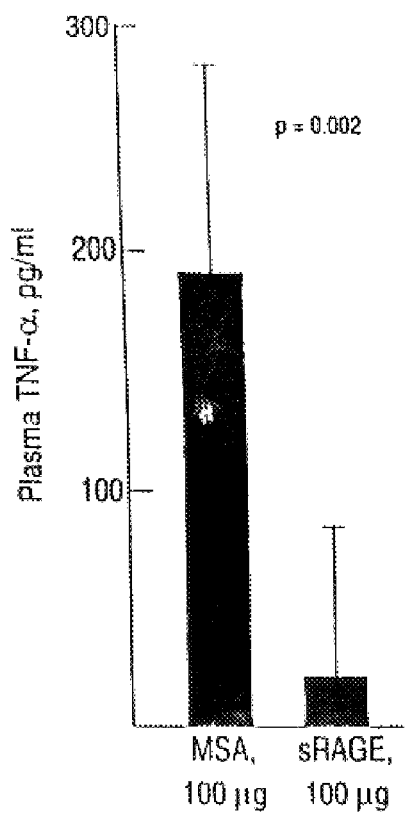

Characteristic of the S100/calgranulin polypeptides is their presence in areas of chronic inflammation, such as human inflammatory bowel diseases (Lugering et al., 1995; Schmid et al., 1995). To test the concept that their interaction with RAGE may be important in the pathogenesis of chronic inflammation, we tested these concepts in a murine model of colitis, IL-10 null mice (Kuehn et al., 1993; Rennick et al., 1997). To test this concept, commencing at age 4 weeks, IL-10 null mice were treated either with MSA or sRAGE, 100 µg per day IP for 6 weeks. At the end of that time, mice were sacrificed and rectosigmoid colon assessed for evidence of inflammation. Although 4/5 mice receiving MSA revealed evidence of submucosal colonic inflammation, composed of lymphocytes, macrophages, eosinophils and plasma cells, only 1/5 mice treated with sRAGE demonstrated patchy inflammation at the base of crypts (Table 3). Consistent with these findings, when colonic tissue was prepared for EMSA, a mean ≈3.7-fold decrease in densitometry units was observed in tissue retrieved from sRAGE-treated IL-10 null mice compared with those receiving MSA (p=0.04; FIG. 10A) Similarly, an ≈8.7-fold decrease in levels of plasma TNF-a were observed in mice treated with sRAGE compared with those receiving MSA (p=0.002; FIG. 10B).

Taken together, these data suggest that inhibition of EN-RAGE/RAGE axis potently suppresses cellular activation and expression of key mediators in models of acute and chronic inflammation.

TABLE 3

Histologic examination of rectosigmoid tissue retrieved from IL-10 null mice. Inflammatory cells are identified as follows: M, monocyte/macrophage; L, lymphocyte; E, eosinophil; and P, plasma cell.

| Mouse # | Condition | Cryptitis | Cellular Infiltrate | Comments |
|---|---|---|---|---|
| 1 | MSA | absent | M | 2 clusters of mononuclear cells identified |
| 2 | MSA | present (Base) | L,P,E,M | patchy submucosal inflammation |
| 3 | MSA | absent | L,P,E,M | patchy submucosal inflammation |
| 4 | MSA | present (Base) | L,P,E,M | focal submucosal inflammation |
| 5 | MSA | absent | none | no inflammation |
| 6 | sRAGE | absent | none | no inflammation |
| 7 | sRAGE | present (Base) | L,P,E,M | patchy submucosal inflammation |
| 8 | sRAGE | absent | none | no inflammation |
| 9 | sRAGE | absent | none | no inflammation |
| 10 | sRAGE | absent | none | non inflammation |

Discussion

The presence of S100/calgranulin polypeptides at sites of acute and chronic inflammation has long been noted. Indeed, assessment of serum levels of MRP8/14 (myeloic-related protein), S100-like molecules, has been suggested as a means to track disease activity in patients with ulcerative colitis, a chronic inflammatory disease of the bowel linked to long-term bowel dysfunction and neoplasia (Lugering et al., 1995). S100/calgranulin molecules bear structural, defining homologies, such as calcium-binding EF-hand domains (Schafer and Heizmann, 1996). Based on these properties, a range of possible intracellular functions for these polypeptides has been postulated, such as alteration of the cytoskeleton and cell shape, signal transduction and, via increased levels of cellular calcium, modulation of phagocytic function, including chemotaxis, phagocytosis, degranulation, and generation of reactive oxygen species (ROIs) (Snyderman and Goetzl, 1981; Smolen et al., 1981; Lew et al., 1984; Sawyer et al., 1985). Indeed, generation of ROIs may represent a further distinct means by which alteration of proinflammatory signalling pathways is initiated by these molecules (Schreck et al., 1992).

Despite the fact that EN-RAGE and related family members lack signal peptides, there is sufficient evidence that these polypeptides readily achieve access to the extracellular space (Suzuki et al., 1983; Shashoua et al., 1984; Schafer and Heizmann, 1996). In this context, previous studies have suggested that members of this family may mediate an array of inflammatory phenomena. For example, upon infusion of CP-10 (chemotactic peptide -10; member of the S100 family) into mice, elicited-macrophages reveal increased scavenger receptor, production of TNF-a, loading of acetylated LDL and foam cell formation, and phagocytosis, as well as decreased production of nitric oxide. Further, upon local footpad injection of CP-10, an intense influx of polymorphonuclear leukocytes, followed by mixed mononuclear cell infiltrate ensues (Hu et al., 1996;

Geczy, 1996; Yen et al., 1997; Kumar et al., 1998). The data presented here extend these findings and suggest that upon recruitment of inflammatory cells to sites of inflammation, these molecules appear to be released and targetted to cellular RAGE. Upon engagement of RAGE, a critical receptor for , members of this family, further cellular stimulation may occur, leading to activation of signalling pathways, modulation of gene expression and amplification of inflammatory events (FIG. 11). These considerations further extend the implications of EN-RAGE-RAGE interaction to chronic inflammatory disorders such as atherosclerosis (Ross, 1999).

Certainly, inflammation is a complex process, with a host of initiating triggers and intermediate participant molecules involved. Often, however, proinflammatory mechanisms may be largely left unchecked, leading to chronic tissue ischemia, cell death, and maladaptive repair responses. Our data suggest a novel paradigm in inflammation; preventing the interaction of EN-RAGEs with RAGE may attenuate an essential amplification mechanism of the inflammatory response via blockade of central signalling pathways leading to cytokine expression. Our data do not exclude the involvement of other receptors for these molecules. In this context, future studies must also determine the extent to which other distinct members of the S100/calgranulin family, beyond EN-RAGE and S100B, bear capacity to interact with RAGE. However, in two studied to date, one more calgranulin-like (EN-RAGE), and the other more S-100-like (S100B),RAGE appears to be a central cellular interaction site. Indeed, our finding that administration of sRAGE, anti-EN-RAGE $F(ab')_2$, anti-RAGE $F(ab')_2$ or anti-EN-RAGE+anti-RAGE $F(ab')_2$, significantly abrogates generation of key inflammatory mediators such as TNF-a and IL-2, strongly suggests a pivotal role for the interaction of EN-RAGE and related family members with RAGE in the inflammatory phenotype.

The present findings expand the context of RAGE as a distinct member of the immunoglobulin superfamily of cell surface molecules by virtue of its unique panel of ligands, with implications in both development and pathophysiologically-relevant states (Schmidt et al., 1998). The identification of amphoterin as a ligand for RAGE (Rauvala and Pihlaskari, 1987; Parkkinen et al., 1993; Hori et al., 1995) suggested a role for RAGE in neurite outgrowth in the developing central nervous system (CNS). Consistent with this concept, expression of neuronal amphoterin and RAGE are strikingly increased and co-localized in developing neurons of the rat CNS (Hori et al., 1995). In in vitro studies, neurite outgrowth of cultured rat embryonic neurons was inhibited specifically on amphoterin-coated matrices by blockade of RAGE, employing either soluble RAGE (sRAGE) or anti-RAGE $F(ab')_2$ fragments. Of note, the observation that RAGE reacts with amphoterin in developing neurons to mediate neurite outgrowth has striking parallels in the biology of the S100 family. Certain members of the latter group, such as S100B mediate neurite outgrowth (Kligman and Marshak, 1985; Marshak, 1990; Barger et al., 1992).

Subsequent to development, the expression of both neuronal amphoterin and RAGE decrease in homeostasis (Hori et al., 1995). However, upon accumulation of amyloid-β peptide in Alzheimer disease.(AD) brain, RAGE expression is enhanced, particularly in affected neurons and vasculature (Yan et al., 1996; Mackic et al, 1998). Studies employing cultured neurons and neuronal-like cells suggest that the interaction of amyloid-β peptide with RAGE mediates neuronal stress and toxicity and activation of microglia, the latter leading to increased generation of macrophage-colony stimulating factor, a potential means, we speculate, to trigger localized inflammatory responses in affected brain, thereby exacerbating neuronal toxicity (Yan et al., 1997). The enhanced expression of neuronal and vascular RAGE which co-localizes with sites of amyloid-β peptide in brain of human subjects with Alzheimer's disease further suggests that this interaction may be highly-relevant in vivo. Studies are underway to elucidate the importance of this interaction employing mice in whom levels and RAGE and amyloidβ peptide have been genetically-enhanced within neurons of the CNS.

In homeostasis, we have observed that levels of RAGE in a wide range of cell types are quite low (Brett et al., 1993; Schmidt et al., 1995a). The implications of this are not entirely clear; however, in other studies, we have demonstrated that administration of soluble RAGE to adult diabetic mice over long periods of time (up to six months) has no adverse effects (unpublished observations, D. Stern and A. M. Schmidt) Indeed, in the setting of diabetes, salutary effects of administration of sRAGE have been noted.

In diabetic tissue, the expression of RAGE is highly-upregulated in tissues such as the vasculature and co-localizes with high levels of the products of nonenzymatic glycation and oxidation, AGEs (Schmidt et al., 1995a; Park et al., 1998). We hypothesize that AGE-RAGE interaction and ensuing chronic cellular perturbation underlie, at least in part, the long-term vascular, neural and inflammatory cell complications of this disorder that impart debilitating consequences (Schmidt et al., 1993; Schmidt et al., 1994; Wautier et al., 1994; Schmidt et al., 1995b; Wautier et al., 1996; Schmidt et al., 1996; Miyata et al., 1996). Consistent with this, administration of sRAGE to diabetic rodents reverses vascular hyperpermeability and suppresses accelerated atherosclerosis (Wautier et al., 1996; Park et al., 1998).

Based on these observations, the extent to which EN-RAGEs contribute to inflammatory events and cellular dysfunction from disorders ranging from diabetes and renal failure to Alzheimer's disease, for example, raises a series of intriguing questions; future studies will address such possibilities in transgenic murine models.

Our present findings thus extend the concept that RAGE is an important molecule in settings in which its ligands accumulate. The characterization of the RAGE promoter, in which multiple potential DNA binding sites exist for a variety of transcription factors capable of altering host phenotype, such as NF-kB, NF-IL-6, g-IRE, Sp1, AP2, etc (Li and Schmidt, 1997; Li et al., 1998) were identified, strongly suggests that RAGE is a versatile gene, responsive to a distinct array of environmental signals. Furthermore, localization of the gene encoding human RAGE to chromosome six within the Major Histocompatibility Complex suggests that RAGE is involved in the host response, from development to pathophysiologically-important disorders (Sugaya et al., 1994).

Taken together, identification of EN-RAGE and EN-RAGE-like molecules as ligands for RAGE thus defines the biologic relevance of S100/calgranulin polypeptides and the immunoglobulin superfamily molecule RAGE. Our demonstration that blockade of EN-RAGE, RAGE and their interaction effectively arrests cellular activation, identifies these mediators as novel, proximal targets for anti-inflammatory strategies designed to quench exaggerated inflammatory responses, thereby limiting tissue injury.

References

Andersson, K. B., Sletten, K., Berntzen, H. B., Dale, I., Brandtzaeg, P., Jellum, E., and Fagerhol, M. K. (1988). The leucocyte L1 protein: identity with the cystic fibrosis antigen and the calcium-binding MRP-8 and MRP-14 macrophage components. Scand. J. Immunol.28, 241–245.

Barger, S. W., Wolchok, S. R., Van Eldik, L. J. (1992) Disulfide-linked S100B dimers and signal transduction. Biochim. Biophys. Acta 1160, 105–112.

Brett, J., Schmidt, A-M., Zou, Y-S., Yan, S-D., Weidman, E., Pinsky, D., Neeper, M., Przysiecki, M., Shaw, A., Migheli, A., and Stern, D. (1993) Tissue distribution of the receptor for advanced glycation endproducts (RAGE): expression in smooth muscle, cardiac myocytes, and neural tissue in addition to the vasculature. Am. J. Pathol. 143, 1699–1712.

Brownlee, M., Cerami, A., and Vlassara, H. (1988) Advanced glycosylation endproducts in tissue and the biochemical basis of diabetic complications. N. Engl. J. Med.318, 1315–1320.

Dell'Angelica, E. C., Schleicher, C. H., and Santome J. A. (1994). Primary structure and binding properties of calgranulin C, a novel S100-like calcium-binding protein from pig granulocytes. J. B. C.269, 28929–28936.

Dunn, C. J., Galinet, L. A., Wu, H., Nugent, R. A., Schlachter, S. T., Staite, N. D., Aspar, D. G., Elliott, G. A., Essani, N. A., Rohloff, N. A., and Smith, R. J. (1993). Demonstration of novel anti-arthritic ant anti-inflammatory effects of Diphosphonates. J Pharm Ex Therap. 266, 1691–1698.

Geczy, C. (1996). Regulation and proinflammatory properties of chemotactic protein, CP-10. Biochimica et Biophysica Acta 1313, 246–252.

Gottsch, J. D., Stark, W. J., and Liu, S. H. (1997). Cloning and sequence analysis of human and bovine corneal antigen (CO-Ag) cDNA: Identification of Host-Parasite protein calgranulin C. Tr.Am.Opthal.Soc. XCV, 111–129.

Gottsch, J. D., and Liu, S. H. (1998). Cloning and expression of human corneal calgranulin C (CO—Ag). Current Eye Research 17, 870–874.

Hitomi, H., Yamaguchi, K., Kikuchi, Y., Kimura, T., Maruyama, K., and Nagasaki, K. A novel calcium-binding protein in amniotic fluid, CAAF1: its molecular cloning and tissue distribution. (1996). J. Cell Science 109, 805–815.

Hu, S. P., Harrison, C., Xu, K., Cornish, C. J., and Geczy, C. L. (1996). Induction of the chemotactic S100 protein, CP-10, in monocyte/macrophages by lipopolysaccharide. Blood 87, 3919–3928.

Hori, O., Brett, J., Slattery, T., Cao, R., Zhang, J., Chen, J., Nagashima, M., Nitecki, D., Morser, J., Stern, D., and Schmidt, A. M. (1995). The receptor for advanced glycation endproducts (RAGE) is a cellular binding site for amphoterin: mediation of neurite outgrowth and coexpression of RAGE and amphoterin in the developing nervous system. J.Biol.Chem. 270, 25752–25761.

Ilg, E. C., Troxler, H., Buergisser, D. M., Kuster, T., Markert, M., Guignard, F., Hunziker, P., Birchler, N., and Heinzmann, C. W. (1996). Amino acid sequence determination of human S100A12 (p6, Calgranulin C, CGRP, CAAF1) by tandem mass spectrometry. Biochem Biophys Research Comm. 225, 146–150.

Kligman, D., and Marshak, D. R. (1985) Isolation and characterization of a neurite extension factor from bovine brain. Proc. Natl. Acad. Sci. USA 82, 7136–7139.

Klotz, I., and Hunston, D. (1984) Mathematical models for ligand-receptor binding. J. Biol. Cehm. 259, 10060–10062.

Kumar, R. K., Harrison, C. A., Cornish, C. J., Kocher, M., and Geczy, C. L. (1998). Immunodetection of the murine chemotactic protein CP-10 in Bleomycin-induced pulmonary injury. Pathology 30, 51–56.

Kuehn, R., Loehler, J., Rennick, D., Rajewsky, K., and Mueller, W. (1993). Interleukin-10-deficient mice develop chronic enterocolitis. Cell 75, 263–274.

Lander, H. L., Tauras, J. M., Ogiste, J. S., Moss, R. A., and A. M. Schmidt. (1997) Activation of the Receptor for Advanced Glycation Endproducts triggers a MAP Kinase pathway regulated by oxidant stress. J. Biol. Chem. 272, 17810–17814.

Lew, P. D., Wollheim, C. B., Waldvogel. F. A., and Pozzano, T. (1984) Modulation of cytosolic-free calcium transients by changes in intracellular calcium-buffering capacity: correlation with exocytosis and $O_2$-production in human neutrophils. J. Cell. Biol. 99, 1212–1220.

Li, H., Cybulsky, M., Gimbrone, M., and Libby, P. (1993) An atherogenic diet rapidly induces VCAM-1, a cytokine-regulatable mononuclear leukocyte adhesion molecule in rabbit aortic endothelium. Arterioscler. Thromb. 13, 197–204.

Li, J., Qu, W., and A. M. Schmidt. (1998) Sp1 binding elements in the promoter of RAGE are essential for amphoterin-mediated gene expression in cultured neuroblastoma cells. J. Biol. Chemistry 273, 30870–30878.

Li, J., and Schmidt, A. M. (1997). Characterization and functional analysis of the promotor of RAGE, the receptor for advanced glycation endproducts. J. Biol. Chem. 271, 16498–16506.

Lugering, N., Stoll, R., Schmid, K. W., Kucharzik, T., Stein, H., Burgmeister, G., Sorg, C., and Domschke, W. (1995). The myeloic related protein MRP8/14 (27E10 antigen) -usefulness as a potential marker for disease activity in ulcerative colitis and putative biological function. Europ. J. of Clin. Invest. 25, 659–664.

Mackic, J. B., Stins, M., McComb, J. G., Calero, M., Ghiso, J., Kim, K. S., Yan, S. D., Stern, D., Schmidt, A. M., Frangione, B., and Zlokovic, B. V. (1998) Human blood-brain barrier receptors for Alzheimer's amyloid-β1-40: asymmetrical binding, endocytosis, and transcytosis at the apical side of brain microvascular endothelial cell monolayer. J. Clin. Invest. 102, 734–743.

Madson, P. (1991). Molecular cloning, occurrence and expression of a novel partially secreted protein "psoriasin" that is highly up-regulated in psoriatic skin. J. Invest. Dermatol. 97, 701–712.

Marshak, D. R. (1990) S100B as a neurotrophic factor. Progress Brain Res. 86, 169–181.

Marti, T., Erttmann, K. D., and Gallin, M. Y. (1996). Host-parasite interaction in human onchocerciasis: identification and sequence analysis of a novel human calgranulin. Biochem Biophys Research Comm. 221, 454–458

Miyata, T., O. Hori, J. H. Zhang, S. D. Yan, L. Ferran, Y. Iida, and A. M. Schmidt. (1996a) The Receptor for Advanced Glycation Endproducts (RAGE) mediates the interaction of AGE-$b_2$-Microglobulin with human mononuclear phagocytes via an oxidant-sensitive pathway: implications for the pathogenesis of dialysis-related amyloidosis. J. Clin. Invest. 98, 1088–1094.

Miyata, T., Taneda, S., Kawai, R., Ueda, Y., Horiuchi, S., Hara, M., Maeda, K., and Monnier, V. M. (1996b) Identification of pentosidine as a native structure for advanced glycation end products in $β_2$-microglobulin-containing amyloid fibrils in patients with dialysis-related amyloidosis. Proc. Natl. Acad. Sci. U.S.A. 93, 2353–2358.

Neish, A. S., Williams, A. J., Palmer, H. J., Whitley, M. Z., and Collins, T. (1992) Functional analysis of the human vascular cell adhesion molecule-1 promoter. J. Exp. Med. 176, 1583–1593.

Neeper, M., Schmidt, A. M., Brett, J., Yan, S. D., Wang, F., Pan, Y. C., Elliston, K., Stern, D., and Shaw, A. (1992). Cloning and expression of RAGE: a cell surface receptor for advanced glycosylation end products of proteins. J. Biol.Chem. 267, 14998–15004.

Odink, K., Cerletti, N., Brueggen, J., Clerc, R. G., Tarcasy, L., Zwadlo, G., Gerhards, G., Schlegel, R., and Sorg, C. (1987). Two calcium-binding proteins in infiltrate macrophages of rheumatoid arthritis. Nature 330, 80–82.

Park, L., Raman, K. G., Lee, K. J., Yan, L., Ferran, L. J., Chow, W. S., Stern, D., and Schmidt, A. M. (1998) Suppression of accelerated diabetic atherosclerosis by soluble Receptor for AGE (sPAGE). Nature Medicine 4, 1025–1031.

Parkkinen, J., Raulo, E., Merenmies, J., Nolo, R., Kagander, E. O., Baumann, M., and Rauvala, H. (1993) Amphoterin, the 30-kDa protein in a family of HMG1-type polypeptides. Enhanced expression in transformed cells, leading edge localization, and interactions with plasminogen activation. J. Biol. Chem. 268, 19726–19738.

Rauvala, H., and Pihlaskari, R.(1987) Isolation and some characteristics of an adhesive factor of brain that enhances neurite outgrowth in central neurons. J. Biol. Chem. 262, 16625–16635.

Reddy, S., Bichler, J., Wells-Knecht, K. J., Thorpe, S. R., and Baynes, J. W. (1995) $N^e$ (Carboxymethyl)lysine is a dominant Advanced Glycation Endproduct (AGE) antigen in tissue proteins. Biochemistry 34, 10872–10878.

Rennick, D. M., Fort, M., and Davidson N. J. ( 1997). Studies with IL-10-/-mice: an overview. J. Leuc. Biol. 61, 389–396.

Richardson, M., Hadcock, S., DeReske, M., and Cybulsky, M. (1994) Increased expression in vivo of VCAM-1 and E-selectin by the aortic endothelium of normolipemic and hyperlipidemic diabetic rabbits. Arterioscler. Thromb. 14, 760–769.

Ross, R. Atherosclerosis—an inflammatory disease. (1999) N. Engl. J. Med. 340, 115–126.

Sawyer, D. W., Sullivan, J. A., and Mandell, G. L. (1985) Intracellular free calcium localization in neutrophils during phagocytosis. Science 230, 663–666.

Schafer, B. W., and Heinzmann, C. W. (1996). The S100 family of EF-hand calcium-binding proteins: functions and pathology. TIBS 21, 134–140.

Schmid, K. W., Lugering, N., Stoll, R., Brinkbaumer, P., Winde, G., Domschke, W., Bocker, W., and Sorg, C. (1995). Immunohistochemical demonstration of calcium-binding proteins MRP8 and MRP 14 and their heterodimer (27E10 antigen) in Crohns disease. Human Pathology 26, 334–337.

Schmidt, A. M., Vianna, M., Gerlach, M., Brett, J., Ryan, J., Kao, J., Esposito, C., Hegarty, H., Hurley, W., Clauss, M., Wang, F., Pan, Y. C., Tsang, T. C., and Stern, D. (1992) Isolation and characterization of binding proteins for advanced glycosylation endproducts from lung tissue which are present on the endothelial cell surface. J. Biol. Chem. 267, 14987–14997.

Schmidt, A. M., Yan, S. D., Brett, J., Mora, R., and Stern, D. Regulation of mononuclear phagocyte migration by cell surface binding proteins for advanced glycosylation endproducts. (1993) J. Clin. Invest. 92, 2155–2168.

Schmidt, A-M., Hasu, M., Popov, D., Zhang, J-H., Yan, S-D., Brett, J., Cao, R., Kuwabara, K., Costache, G., Simionescu, N., Simicnescu, M., and Stern, D. (1994) The receptor for Advanced Glycation Endproducts (AGEs) has a central role in vessel wall interactions and gene activation in response to AGEs in the intravascular space. PNAS(USA) 91, 8807–8811.

Schmidt, A. M., Yan, S. D. and D. Stern. (1995a) The Dark Side of Glucose (News and Views). Nature Medicine 1, 1002–1004.

Schmidt, AM., O Hori, J. Chen, J. F. Li, J. Crandall, J. Zhang, R. Cao, S. D. Yan, J. Brett and D. Stern. (1995b) Advanced glycation endproducts interacting with their endothelial receptor induce expression of vascular cell adhesion molecule-1 (VCAM-1): a potential mechanism for the accelerated vasculopathy of diabetes. J. Clin. Invest. 96, 1395–1403.

Schmidt, A. M., E. Weidman, E. Lalla, S. D. Yan, O. Hori, R. Cao, J. Brett, and I. Lamster. (1996) Advanced Glycation Endproducts induce oxidant stress in the gingiva: a potential mechanism underlying accelerated periodontal disease associated with diabetes. J. Periodontal Res. 31, 508–515.

Schmidt, A. M., Wautier, J-l., Stern, D., and Yan S. D. (1998). RAGE: a receptor with a taste for multiple ligands and varied pathophysiologic states. Hormones and Signaling 1, 41–63.

Schreck, R., Grassmann, R., Fleckenstein, B., and Baeuerle, P. A. Antioxidants selectively suppress activation of NF-kappa B by human T-cell leukemia virus type 1 Tax protein. (1992) 66, 6288–6293.

Schreiber, S., Nikolaus, S., and Hampe, J. (1998). Activation of NF-kB in inflammatory bowel disease. Gut 42, 477–484.

Sell, D., and Monnier, V. (1989) Structure elucidation of a senescence cross-link from human extracellular matrix; implication of pentoses in the aging process. J. Biol. Chem. 264, 21597–21602.

Shashoua, V. E., Hesse, G. W., and Moore B. W. (1984). Proteins of the brain extracellular fluid: Evidence for release of S100 protein. J. Neurochem. 42, 1536–1541.

Smolen, J. E., Korchak, H. M., and Weissmann, G. (1981) The roles of extracellular and intracellular calcium in lysosomal enzyme release and superoxide anion generated by human neutrophils. Biochim. Biophys. Acta 677, 512–520.

Snyderman, R., and Goetzl, E. J. (1981) Molecular and cellular mechanisms of leukocyte chemotaxis. Science 213, 830–837.

Sugaya, K., Fukagawa, T., Matsumoto, K., Mita, K., Takahashi, E., Ando, A., Inoko, H., and Ikemura, T. Three genes in the human MHC class III region near the junction with the class II: gene for receptor for advanced glycosylation end products, PBX2 homeobox 2 gene and a notch homolog, human counterpart of mouse mammary tumor gene int-3. (1994) Genomics 23, 408–419.

Suzuki, F., Kato, K., and Nakajima, T. (1983). Enhancement of adipose S100 protein release by catecholamines. J. Biochem. 94, 1707–1710.

Wautier, J-L., M-P. Wautier, A-M. Schmidt, G. M. Anderson, C. Zoukourian, L. Capron, O. Chappey, S-D. Yan, J. Brett, P-J. Guillausseau, and D. Stern. (1994) Advanced glycation endproducts (AGEs) on the surface of diabetic red cells bind to the vessel wall via a specific receptor inducing oxidant stress in the vasculature: a link between surface-associated AGEs and diabetic complications. PNAS(USA) 91, 7742–7746.

Wautier, J-L., Zoukourian, C., O. Chappey, M-P. Wautier, P-J. Guillausseau, R. Cao, O. Hori, D. Stern, and A. M. Schmidt. (1996) Receptor-mediated endothelial cell dysfunction in diabetic vasculopathy: soluble receptor for advanced glycation endproducts blocks hyperpermeability. J. Clin. Invest. 97, 238–243.

Yamamura, T., Hitomi, J., Nagasaki, K., Suzuki, M., Takahashi, E., Saito, S., Tsukada, T., and Yamaguchi, K. (1996). Human CAAF1 gene-molecular cloning, gene structure, and chromosome mapping. Biochem Biophys Res Comm 221, 356–360.

Yan, S. D., Chen, X., Fu, J., Chen, M., Zhu, H., Roher, A., Slattery, T., Nagashima, M., Morser, J., Migheli, A., Nawroth, P., Godman, G., Stern, D., and Schmidt, A. M. (1996). RAGE and amyloid beta peptide neurotoxicity in Alzheimer's disease. Nature 382, 685–691.

Yan, S-D., Schmidt A-M., Anderson, G., Zhang, J., Brett, J., Zou, Y-S., Pinsky, D., and Stern, D. (1994) Enhanced cellular oxidant stress by the interaction of advanced glycation endproducts with their receptors/binding proteins. j. Biol. Chem. 269, 9889–9897.

Yan, S. D., Zhu, H., Fu, J., Yan S. F., Roher, A., Tourtellotte, W., Rajavashisth, T., Chen, X., Stern, D., and Schmidt A. M. (1997). Amyloid-beta peptide-RAGE interaction elicits neuronal expression of M-CSF: a proinflammatory pathway in Alzheimer's disease. Proc.Natl.Acad.Sci.94, 5296–5301.

Yen, T., Harrison, C. A., Devery, J. M., Leong, S., Iismaa, S. E., Yoshimura, T., and Geczy, C. L. (1997). Induction of the S100 chemotactic protein, CP-10, in murine microvascular endothelial cells by proinflammatory stimuli. Blood 90, 4812–4821.

Wicki, R., Marenholz, I., mischke, D., Schaefer, B. W., Heinzmann, C. W. (1996). Characterization of the human S100A12 (calgranulin C, p6, CAAF1, CGRP) gene, a new member of the S100 gene cluster on chromosome 1q21. Cell Calcium 20, 459–464.

Zimmer, D. B., Cornwall, E. H., Landar, A., and Song, W. (1995). The S100 protein family: history, function, and expression. Brain Research Bulletin 37, 417–429.

What is claimed is:

1. A method for determining whether a compound is capable of inhibiting the interaction of an EN-RAGE peptide with a RAGE peptide, which comprises:
   (a) admixing:
      (i) a RAGE peptide or an sRAGE peptide or a fragment of either thereof,
      (ii) an EN-RAGE peptide or a fragment thereof, and
      (iii) the compound;
   (b) measuring the level of interaction between the peptide of step (a) (i) and the peptide of step (a) (ii), and
   (c) Comparing the amount of interaction meausred in step (b) with the amount measured between the petpide of step (a) (i) and the peptide of step (a) (ii) in the absence of the compound, thereby determining whether the compound is capable of inhibiting the interaction of the EN-RAGE peptide with the RAGE peptide, wherein a reduction in the amount of interaction in the presence of the compound indicates that the compound is capable of inhibiting the interaction.

2. A method for determining whether a compound is capable of inhibiting the ability of EN-RAGE protein to bind with a second protein which comprises:
   (a) admixing the EN-RAGE protein, the second protein and the compound;
   (b) measuring the amount of binding between the EN-RAGE Protein and the second protean; and
   (c) comparing the amount of binding measured in step (b) with the amount of binding between EN-RAGE and the second protein in the absence of the compound, wherein a reduction in the amount of binding indicates that the compound is capable of inhibiting the ability of EN-RAGE protein to bind with the second protein.

* * * * *